US008334101B2

(12) United States Patent
Latz et al.

(10) Patent No.: US 8,334,101 B2
(45) Date of Patent: Dec. 18, 2012

(54) INTRACELLULAR DNA RECEPTOR

(75) Inventors: Eicke Latz, Worcester, MA (US); Veit Hornung, Pullach (DE); Katherine A. Fitzgerald, Wellesley, MA (US)

(73) Assignee: University of Massachusetts, Shrewsbury, MA (US)

( * ) Notice: Subject to any disclaimer, the term of this patent is extended or adjusted under 35 U.S.C. 154(b) by 0 days.

(21) Appl. No.: 12/586,662

(22) Filed: Sep. 25, 2009

(65) Prior Publication Data

US 2010/0120894 A1    May 13, 2010

Related U.S. Application Data

(60) Provisional application No. 61/194,449, filed on Sep. 26, 2008.

(51) Int. Cl.
*G01N 33/53* (2006.01)
(52) U.S. Cl. ......................................................... 435/7.1
(58) Field of Classification Search ........................ None
See application file for complete search history.

(56) References Cited

U.S. PATENT DOCUMENTS

| 2005/0239070 A1 | 10/2005 | Von Knebel-Doeberitz et al. |
| 2005/3023070 | 10/2005 | Von Knebel-Doeberitz et al. |
| 2006/0198842 A1 | 9/2006 | Isfort et al. |

OTHER PUBLICATIONS

Choubey et al., "Cytoplasmic localization of the interferon-inducible protein that is encoded by the AIM2 (absent in melanoma) gene from the 200-gene family," FEBS Letters, vol. 474, pp. 38-42 (2000).
Mondini et al., "Role of the Interferon-Inducible Gene IFI16 in the Etiopathogenesis of Systemic Autoimmune Disorders," Ann.N.Y., Acad. Sci., vol. 1110, pp. 47-56 (2007).
International Search Report dated May 13, 2010, 12 pages.

*Primary Examiner* — Michael Pak
(74) *Attorney, Agent, or Firm* — Fish & Richardson P.C.

(57) ABSTRACT

Provided herein are methods of identifying and using compounds that modulate an AIM2 polypeptide-mediated immune response. Further provided herein are methods of treating disease comprising administering to a patient a compound that decreases expression of an AIM2 polypeptide. Further provided herein are methods of providing gene therapy to a patient comprising administering to the patient a gene therapy agent and a compound that decreases expression of an AIM2 polypeptide. In certain embodiments, a compound that decreases expression of an AIM2 polypeptide comprises an siRNA or an shRNA.

20 Claims, 12 Drawing Sheets
(7 of 12 Drawing Sheet(s) Filed in Color)

SEQUENCE LISTING

```
<160> NUMBER OF SEQ ID NOS: 21

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
ctggtgaaaa ggacctctcg                                                  20

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
tgaagtactc attatagtca agggca                                           26

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
ataagcagct ccagctccaa                                                  20

<210> SEQ ID NO 4
```

```
<211> LENGTH: 20
<212> TYPE: DNA
<213> ORGANISM: Artificial Sequence
<220> FEATURE:
<223> OTHER INFORMATION: Primer

<400> SEQUENCE: 4
ctgtctgctg gtggagttca                                               20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
ggccgcatag tcatccttta                                               20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
caacagcatt tcccggtact                                               20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
atgctgcttc gacatctcct                                               20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
aaccaatgcg agatcctgac                                               20

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
cccgaagatc aacacgcttc a                                             21

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
```
cgggaaggtc ctgacggatg a                                                21

<210> SEQ ID NO 11
<211> LENGTH: 19
<212> TYPE: RNA
<213> ORGANISM: Artificial Sequence
<220> FEATURE:
<223> OTHER INFORMATION: Primer

<400> SEQUENCE: 11
gggaguuacu gcuugaaga                                                   19

<210> SEQ ID NO 12
<211> LENGTH: 78
<212> TYPE: PRT
<213> ORGANISM: Homo sapiens

<400> SEQUENCE: 12

Lys Glu Ile Leu Leu Thr Gly Leu Asp Asn Ile Thr Asp Glu Glu
 1               5                  10                  15

Leu Asp Arg Phe Lys Phe Phe Leu Ser Asp Glu Phe Asn Ile Ala Thr
                20                  25                  30

Gly Lys Leu His Thr Ala Asn Arg Ile Gln Val Ala Thr Leu Met Ile
            35                  40                  45

Gln Asn Ala Gly Ala Val Ser Ala Val Met Lys Thr Ile Arg Ile Phe
50                  55                  60

Gln Lys Leu Asn Tyr Met Leu Leu Ala Lys Arg Leu Gln Glu
65                  70                  75

<210> SEQ ID NO 13
<211> LENGTH: 79
<212> TYPE: PRT
<213> ORGANISM: Homo sapiens

<400> SEQUENCE: 13

Lys Lys Ile Leu Leu Leu Lys Gly Phe Glu Leu Met Asp Asp Tyr His
 1               5                  10                  15

Phe Thr Ser Ile Lys Ser Leu Leu Ala Tyr Asp Leu Gly Leu Thr Thr
                20                  25                  30

Lys Met Gln Glu Glu Tyr Asn Arg Ile Lys Ile Thr Asp Leu Met Glu
            35                  40                  45

Lys Lys Phe Gln Gly Val Ala Cys Leu Asp Lys Leu Ile Glu Leu Ala
50                  55                  60

Lys Asp Met Pro Ser Leu Lys Asn Leu Val Asn Asn Leu Arg Lys
65                  70                  75

<210> SEQ ID NO 14
<211> LENGTH: 79
<212> TYPE: PRT
<213> ORGANISM: Homo sapiens

<400> SEQUENCE: 14

Lys Asn Ile Val Leu Leu Lys Gly Leu Glu Val Ile Asn Asp Tyr His
 1               5                  10                  15

Phe Arg Met Val Lys Ser Leu Leu Ser Asn Asp Leu Lys Leu Asn Leu
                20                  25                  30

Lys Met Arg Glu Glu Tyr Asp Lys Ile Gln Ile Ala Asp Leu Met Glu
            35                  40                  45

Glu Lys Phe Arg Gly Asp Ala Gly Leu Gly Lys Leu Ile Lys Ile Phe
50                  55                  60

```
Glu Asp Ile Pro Thr Leu Glu Asp Leu Ala Glu Thr Leu Lys Lys
65                  70                  75
```

<210> SEQ ID NO 15
<211> LENGTH: 79
<212> TYPE: PRT
<213> ORGANISM: Homo sapiens

<400> SEQUENCE: 15

```
Lys Lys Ile Val Leu Leu Lys Gly Leu Glu Val Ile Asn Asp Tyr His
1               5                   10                  15

Phe Arg Ile Val Lys Ser Leu Leu Ser Asn Asp Leu Lys Leu Asn Pro
                20                  25                  30

Lys Met Lys Glu Glu Tyr Asp Lys Ile Gln Ile Ala Asp Leu Met Glu
            35                  40                  45

Glu Lys Phe Pro Gly Asp Ala Gly Leu Gly Lys Leu Ile Glu Phe Phe
        50                  55                  60

Lys Glu Ile Pro Thr Leu Gly Asp Leu Ala Glu Thr Leu Lys Arg
65                  70                  75
```

<210> SEQ ID NO 16
<211> LENGTH: 83
<212> TYPE: PRT
<213> ORGANISM: Homo sapiens

<400> SEQUENCE: 16

```
Gly Leu Cys Arg Leu Ser Thr Tyr Leu Glu Glu Leu Glu Ala Val Glu
1               5                   10                  15

Leu Lys Lys Phe Lys Leu Tyr Leu Gly Thr Ala Thr Glu Leu Gly Glu
                20                  25                  30

Gly Lys Ile Pro Trp Gly Ser Met Glu Lys Ala Gly Pro Leu Glu Met
            35                  40                  45

Ala Gln Leu Leu Ile Thr His Phe Gly Pro Glu Glu Ala Trp Arg Leu
        50                  55                  60

Ala Leu Ser Thr Phe Glu Arg Ile Asn Arg Lys Asp Leu Trp Glu Arg
65                  70                  75                  80

Gly Gln Arg
```

<210> SEQ ID NO 17
<211> LENGTH: 84
<212> TYPE: PRT
<213> ORGANISM: Homo sapiens

<400> SEQUENCE: 17

```
Thr Arg Cys Lys Leu Ala Arg Tyr Leu Glu Asp Leu Glu Asp Val Asp
1               5                   10                  15

Leu Lys Lys Phe Lys Met His Leu Glu Asp Tyr Pro Pro Gln Lys Gly
                20                  25                  30

Cys Ile Pro Leu Pro Arg Gly Gln Thr Glu Lys Ala Asp His Val Asp
            35                  40                  45

Leu Ala Thr Leu Met Ile Asp Phe Asn Gly Glu Glu Lys Ala Trp Ala
        50                  55                  60

Met Ala Val Trp Ile Phe Ala Ala Ile Asn Arg Arg Asp Leu Tyr Glu
65                  70                  75                  80

Lys Ala Lys Arg
```

<210> SEQ ID NO 18
<211> LENGTH: 82
<212> TYPE: PRT

-continued

<213> ORGANISM: Homo sapiens

<400> SEQUENCE: 18

Ala Arg Glu Leu Leu Ala Ala Leu Glu Glu Ser Gln Glu Gln
1               5                   10                  15

Leu Lys Arg Phe Arg His Lys Leu Arg Asp Val Gly Pro Asp Gly Arg
            20                  25                  30

Ser Ile Pro Trp Gly Arg Leu Glu Arg Ala Asp Ala Val Asp Leu Ala
        35                  40                  45

Glu Gln Leu Ala Gln Phe Tyr Gly Pro Glu Pro Ala Leu Glu Val Ala
    50                  55                  60

Arg Lys Thr Leu Lys Arg Ala Asp Ala Arg Asp Val Ala Ala Gln Leu
65                  70                  75                  80

Gln Glu

<210> SEQ ID NO 19
<211> LENGTH: 84
<212> TYPE: PRT
<213> ORGANISM: Homo sapiens

<400> SEQUENCE: 19

Ala Arg Asp Ala Ile Leu Asp Ala Leu Glu Asn Leu Thr Ala Glu Glu
1               5                   10                  15

Leu Lys Lys Phe Lys Leu Lys Leu Leu Ser Val Pro Leu Arg Glu Gly
            20                  25                  30

Tyr Gly Arg Ile Pro Arg Gly Ala Leu Leu Ser Met Asp Ala Leu Asp
        35                  40                  45

Leu Thr Asp Lys Leu Val Ser Phe Tyr Leu Glu Thr Tyr Gly Ala Glu
    50                  55                  60

Leu Thr Ala Asn Val Leu Arg Asp Met Gly Leu Gln Glu Met Ala Gly
65                  70                  75                  80

Gln Leu Gln Ala

<210> SEQ ID NO 20
<211> LENGTH: 84
<212> TYPE: PRT
<213> ORGANISM: Homo sapiens

<400> SEQUENCE: 20

Met Gly Phe Asn Leu Gln Ala Leu Leu Glu Gln Leu Ser Gln Asp Glu
1               5                   10                  15

Leu Ser Lys Phe Lys Tyr Leu Ile Thr Thr Phe Ser Leu Ala His Glu
            20                  25                  30

Leu Gln Lys Ile Pro His Lys Glu Val Asp Lys Ala Asp Gly Lys Gln
        35                  40                  45

Leu Val Glu Ile Leu Thr Thr His Cys Asp Ser Tyr Trp Val Glu Met
    50                  55                  60

Ala Ser Leu Gln Val Phe Glu Lys Met His Arg Met Asp Leu Ser Glu
65                  70                  75                  80

Arg Ala Lys Asp

<210> SEQ ID NO 21
<211> LENGTH: 84
<212> TYPE: PRT
<213> ORGANISM: Homo sapiens

<400> SEQUENCE: 21

Lys Arg Glu Ala Ile Leu Lys Val Leu Glu Asn Leu Thr Pro Glu Glu

-continued

```
              1               5              10              15
Leu Lys Lys Phe Lys Met Lys Leu Gly Thr Val Pro Leu Arg Glu Gly
             20              25              30

Phe Gly Arg Ile Pro Arg Gly Ala Leu Gly Gln Leu Asp Ile Val Asp
             35              40              45

Leu Thr Asp Lys Leu Val Ala Ser Tyr Tyr Glu Asp Tyr Ala Ala Glu
             50              55              60

Leu Val Val Ala Val Leu Arg Asp Met Arg Met Leu Glu Glu Ala Ala
 65              70              75              80

Arg Leu Gln Arg
```

INTRACELLULAR DNA RECEPTOR

CROSS-REFERENCE TO RELATED APPLICATIONS

This application claims priority to U.S. Provisional Patent application No. 61/194,449 filed Sep. 26, 2008, the contents of which are incorporated by reference herein in their entirety.

TECHNICAL FIELD

Provided herein are methods of identifying and using compounds that modulate an AIM2 polypeptide-mediated immune response. Also provided herein are methods of treating disease comprising administering to a patient or animal a compound that decreases expression of an AIM2 polypeptide. Also provided herein are methods of providing gene therapy to a patient or animal comprising administering to the patient or animal a gene therapy agent and a compound that decreases expression of an AIM2 polypeptide. In certain embodiments, a compound that decreases expression of an AIM2 polypeptide comprises an siRNA or an shRNA.

BACKGROUND

The innate immune system is a universal and ancient form of host defense mechanism that senses non-self nucleic acids via germ-line encoded pattern recognition receptors. The innate immune system includes cells and mechanisms that defend the host from infection by other organisms, in a non-specific manner. Compared to the almost limitless diversity of the adaptive immune system, innate immunity is generally considered to include only a limited number of stereotyped responses by few cell types. The innate immune system produces proinflammatory cytokines and chemokines that not only play a role in clearing pathogens and reducing their spread, but also in helping shape the downstream adaptive immune responses. Cytoplasmic DNA triggers the innate immune response and triggers type I IFN gene transcription and caspase-1-mediated processing of IL-1beta. However, little is known about molecular receptors for cytoplasmic DNA.

SUMMARY

Provided herein are compositions and methods based, at least in part, on the discovery that AIM2, also known as PISA, is involved in the innate immune system response. Methods of identifying and using compounds that modulate an AIM2 polypeptide-mediated immune response are also provided herein.

In certain embodiments, methods provided herein comprise identifying a compound that modulates an AIM2 polypeptide-mediated immune response by providing a cell that expresses an AIM2 polypeptide, contacting the cell with a test compound to generate a test sample, incubating the test sample under conditions and for a time sufficient such that a cellular characteristic of an AIM2 polypeptide-mediated immune response would occur if a reference sample lacking the test compound were incubated under said conditions and for said time, and detecting or measuring the cellular characteristic. In certain embodiments, the cellular characteristic is selected from the group consisting of: cleavage of a pro-IL-1beta polypeptide, expression of NF-kappaB, type I IFN induction, intracellular co-localization of the AIM2 polypeptide and an ASC polypeptide, intracellular co-localization of the AIM2 polypeptide and a cytoplasmic dsDNA, and combinations thereof. In certain embodiments, a change in the detected cellular characteristic compared to a reference cellular characteristic that would be observed in said reference sample indicates that the test compound is a compound that modulates the AIM2-mediated immune response.

In certain embodiments, cleavage of a pro-IL-1beta polypeptide is detected or measured. In certain embodiments, a detected pro-IL-1beta polypeptide is a pro-IL-1beta fusion polypeptide. For example, a detected pro-IL-1beta fusion polypeptide may comprise an epitope tag such as, without limitation, Flag, myc, T7, Glutathione-S-transferase, Yellow Fluorescent Protein (YFP), a Cyan Fluorescent Protein (CFP), Green Fluorescent Protein (GFP), Red Fluorescent Protein (RFP), hemagglutinin.

In certain embodiments intracellular co-localization of an AIM2 polypeptide and an ASC polypeptide is detected or measured. In certain embodiments, an AIM2 polypeptide is labeled, is a fusion polypeptide, and/or is a fluorescent fusion polypeptide. For example, an AIM2 polypeptide may be a fusion protein comprising a Yellow Fluorescent Protein (YFP), a Cyan Fluorescent Protein (CFP), Green Fluorescent Protein (GFP), Red Fluorescent Protein (RFP), or a fluorescent variant thereof. In certain embodiments, an ASC polypeptide is labeled, is a fusion polypeptide, and/or is a fluorescent fusion polypeptide. For example, an ASC polypeptide may be a fusion protein comprising a Yellow Fluorescent Protein (YFP), a Cyan Fluorescent Protein (CFP), Green Fluorescent Protein (GFP), Red Fluorescent Protein (RFP), or a fluorescent variant thereof.

In certain embodiments intracellular co-localization of an AIM2 polypeptide and a cytoplasmic dsDNA is detected or measured. In certain embodiments, an AIM2 polypeptide is labeled, is a fusion polypeptide, and/or is a fluorescent fusion polypeptide. For example, an AIM2 polypeptide may be a fusion protein comprising a Yellow Fluorescent Protein (YFP), a Cyan Fluorescent Protein (CFP), Green Fluorescent Protein (GFP), Red Fluorescent Protein (RFP), or a fluorescent variant thereof. In certain embodiments, a cytoplasmic dsDNA is labeled with a fluorophore. For example, a cytoplasmic dsDNA may be labeled, without limitation, with a fluorophore selected from the group consisting of: fluorescein, 6-FAM, TET, HEX, TAMRA, Texas Red, JOE, Cy5, Cy3, BODIPY FL, Oregon Green 488, and combinations thereof.

In certain embodiments, intracellular co-localization of an AIM2 polypeptide and an ASC polypeptide or intracellular co-localization of an AIM2 polypeptide and a cytoplasmic dsDNA is detected or measured by a method such as fluorescence resonance energy transfer, homogeneous time resolved fluorescence, an amplified luminescent-proximity homogeneous assay, coimmunoprecipitation, fractionation of cellular lysates, an ELISA type assay, or a DNA aptamer technique.

Methods of treating a disease comprising administering to a patient or animal a compound that decreases expression of an AIM2 polypeptide are also provided herein. In certain embodiments, methods of treating disease provided herein comprise administering to a patient or animal siRNA or an shRNA, which siRNA or shRNA decreases expression of an AIM2 polypeptide. In certain embodiments, administration of an siRNA or an shRNA directed against a nucleic acid molecule that encodes an AIM2 polypeptide decreases expression of the AIM2 polypeptide by at least 25%, 30%, 35%, 40%, 45%, 50%, 55%, 60%, 65%, 70%, 75%, 80%, 85%, 90%, 95%, 96%, 97%, 98%, 99%, or more. In certain embodiments, a disease to be treated is rheumatoid arthritis, lupus, or psoriasis.

Methods of treating an infection comprising administering to a patient or animal a compound that decreases expression of an AIM2 polypeptide are also provided herein. In certain embodiments, methods of treating an infection provided herein comprise administering to a patient or animal siRNA or an shRNA, which siRNA or shRNA decreases expression of an AIM2 polypeptide. In certain embodiments, administration of an siRNA or an shRNA directed against a nucleic acid molecule that encodes an AIM2 polypeptide decreases expression of the AIM2 polypeptide by at least 25%, e.g., by at least 30%, 35%, 40%, 45%, 50%, 55%, 60%, 65%, 70%, 75%, 80%, 85%, 90%, 95%, 96%, 97%, 98%, 99%, or more. In certain embodiments, an infection to be treated is a bacterial infection caused by bacterial pathogens such as, without limitation, *Shigella* spp., *Francisella* spp. *Chlamyida* spp. *Listeria monocytogenes*, *Mycobacterium tuberculosis*, *Mycobacterium leprae*, *Mycobacterium avium intracellulare*, *Brucella* spp., *Salmonella* spp., *Legionella*, or *Rickettsia*. In certain embodiments, an infection to be treated is a viral infection caused by a viral pathogen such as, without limitation, a member of the viral family Adenoviridae, Picornaviridae, Herpesviridae, Hepadnaviridae, Flaviviridae, Retroviridae, Orthomyxoviridae, Paramyxoviridae, Papovaviridae, Rhabdoviridae or Togaviridae.

Methods of providing gene therapy to a patient or animal comprising administering to the patient or animal a gene therapy agent and a compound that decreases expression of an AIM2 polypeptide are also provided herein. For example, a gene therapy agent can be a viral vector that has been engineered to contain a gene of interest. In certain embodiments, a viral vector can be a retrovirus, a herpes simplex virus, an adenovirus, or an adeno-associated virus. In certain embodiments, a compound that decreases expression of an AIM2 polypeptide comprises an siRNA or an shRNA. In certain embodiments, methods of providing gene therapy provided herein comprise administration of an siRNA or an shRNA directed against a nucleic acid molecule that encodes an AIM2 polypeptide such that expression of the AIM2 polypeptide is decreased by at least 25%, e.g., by at least 30%, 35%, 40%, 45%, 50%, 55%, 60%, 65%, 70%, 75%, 80%, 85%, 90%, 95%, 96%, 97%, 98%, 99%, or more.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

DESCRIPTION OF CERTAIN EMBODIMENTS

Figure 1:
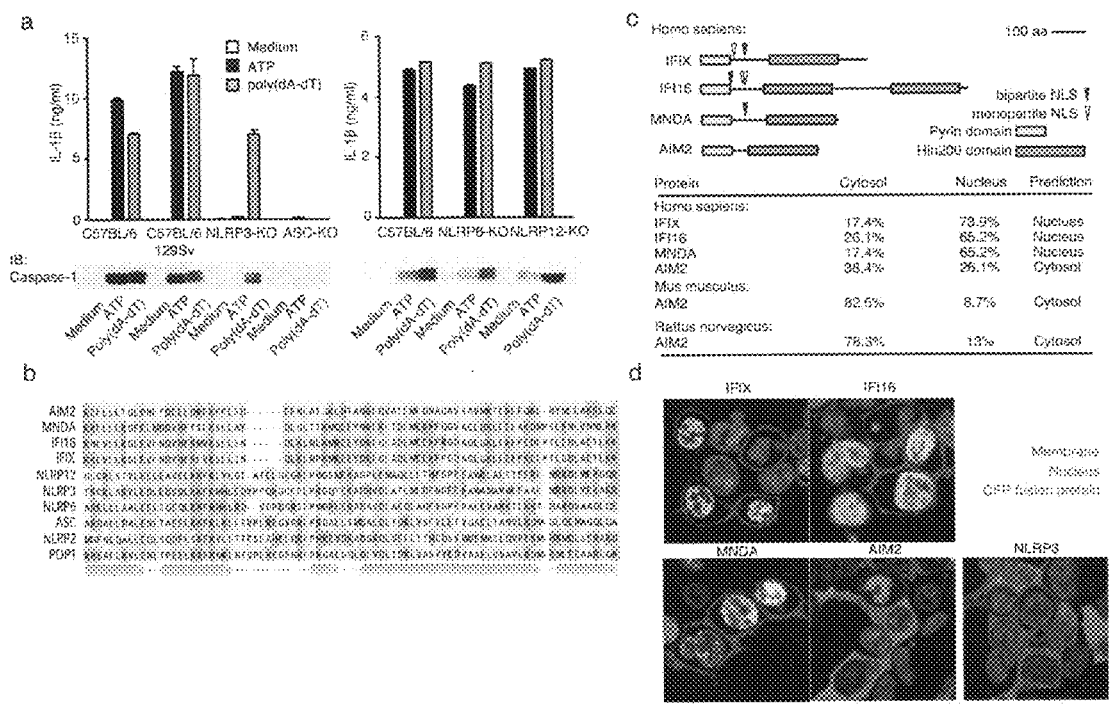
FIG. 1 shows that poly(dA-dT)-mediated inflammasome activation involves ASC, but is independent of NLRP3, NLRP6 and NLRP12. a) Macrophages from either wild type, ASC, −/−, NLRP3−/−, NLRP6−/− or NLRP12−/− mice were LPS-primed and then stimulated with ATP or transfected with poly(dA-dT). After 6 hours, supernatants were assessed for IL-1beta by ELISA and for cleaved caspase-1 by immunoblot. b) A multiple sequence alignment of human PYHIN and select NLR PYD domains was generated using MUSCLE. The following sequences are shown in FIG. 1b: AIM2 (5'-KEILLLTGLDNITDEELDRFKFFLS-DEFNIATGKLHTANRIQVATLMIQNAGAVSAVMKTI RIFQKLNYMLLAKRLQE-3' [SEQ ID NO: 12]), MNDA (5'-KKILLLKGFELMDDYHFTSIKSLLAY-DLGLTTKMQEEYNRIKITDLMEKKFQGVACLDK LIELAKDMPSLKNLVNNLRK-3' [SEQ ID NO: 13]), IFI16 (5'-KNIVLLKGLEVINDYHFRMVKSLL-SNDLKLNLKMREEYDKIQIADLMEEKFRGDAGLG KLIKIFEDIPTLEDLAETLKK-3' [SEQ ID NO: 14]), IFIX (5'-KKIVLLKGLEVINDYHFRIVKSLL-SNDLKLNPKMKEEYDKIQIADLMEEKFPGDAGLGKL IEFFKEIPTLGDLAETLKR-3' [SEQ ID NO: 15]), NLRP12 (5'-GLCRLSTYLEELEAVELKKFKLYLG-TATELGEGKIPWGSMEKAGPLEMAQLLITHFGPE EAWRLALSTFERINRKDLWERGQR-3' [SEQ ID NO: 16]), NLRP3 (5'-TRCKLARYLEDLEDVDLKKFKMHLE-DYPPQKGCIPLPRGQTEKADHVDLATLMIDFNG EEKAWAMAVWIFAAINRRDLYEKAKR-3' [SEQ ID NO: 17]), NLRP6 (5'-ARELLLAALEELSQEQLKRFRHKLRD-VGPDGRSIPWGRLERADAVDLAEQLAQFYGPEP ALEVARKTLKRADARDVAAQLQE-3' [SEQ ID NO: 18]), ASC (5'-ARDAILDALENLTAEELKKFKLKLLSV-PLREGYGRIPRGALLSMDALDLTDKLVSFYLET YGA-ELTANVLRDMGLQEMAGQLQA-3' [SEQ ID NO: 19]), NLRP2 (5'-MGFNLQALLEQLSQDELSKFKYLITTFS-LAHELQKIPHKEVDKADGKQLVEILTTHCDSY WVE-MASLQVFEKMHRMDLSERAKD-3' [SEQ ID NO: 20]), POP1 (5'-KREAILKVLENLTPEELKKFKMKLGTV-PLREGFGRIPRGALGQLDIVDLTDKLVASYYED YAAELVVAVLRDMRMLEEAARLQR-3' [SEQ ID NO: 21]). c) The domain structures of the four human PYHIN proteins are depicted, with predicted monopartite or bipartite nuclear localization signals indicated. The predicted subcellular localization was calculated for the four human PYHIN proteins and for murine and rat AIM2 (SEQ ID NO:12) and is shown in the lower panel. d) 293T cells overexpressing CFP-tagged PYHIN-1, PYHIN-2, PYHIN-3, AIM2 or NLRP3 (shown in green in the original) were analyzed by confocal microscopy. Membranes were stained with fluorescent choleratoxin (shown in blue in the original) and nuclei with DRAQ5 dye (shown in red in the original). Data from one representative experiment out of three are shown (a,d).

Provided herein are methods of identifying and using compounds that modulate an AIM2 polypeptide-mediated immune response. The presently disclosed compositions and methods are based, at least in part, on the discovery that AIM2 is involved in the innate immune system response that protects against cytoplasmic DNA.

Additionally, provided herein are methods of treating disease comprising administering to a patient or animal a compound that decreases expression of an AIM2 polypeptide. Additionally, provided herein are methods of providing gene therapy to a patient or animal comprising administering to the patient or animal a gene therapy agent and a compound that decreases expression of an AIM2 polypeptide. In certain embodiments, a compound that decreases expression of an AIM2 polypeptide comprises an siRNA or an shRNA.

Innate Immune Response

In contrast to the adaptive immune response, the innate immune system works to defend a host from infection in a non-specific manner. Thus, cells of the innate system recognize and respond to pathogens. However, unlike the adaptive immune system, the innate immune system does not confer long-lasting or protective immunity to the host. The innate immune system is nevertheless useful in that it provides immediate defense against infection. The innate immune system is widespread in and is found in all classes of plant and animal life.

In the innate immune system, RNA is sensed via Toll-like receptor (TLR)-3, -7 and -8 or by the cytoplasmic RNA helicases RIG-I and MDA-5 (E. Meylan, et al., Nature 442 (7098), 39 (2006); O. Takeuchi and S. Akira, Curr Opin Immunol 20 (1), 17 (2008)). Little is known about sensors for cytoplasmic DNA, which when delivered to the cytoplasm triggers type I IFN gene transcription and caspase-1-mediated processing of IL-1beta. Recent evidence indicates that in addition to TLR9, cells express one or more cytosolic DNA sensors, which trigger potent antiviral and/or inflammatory responses (Ken J. Ishii and Shizuo Akira, Trends in immunology 27 (11), 525 (2006); K. J. Ishii, et al., Nature 451 (7179), 725 (2008); D. B. Stetson and R. Medzhitov, Immunity 24 (1), 93 (2006); D. A. Muruve, et al., Nature 452 (7183), 103 (2008)). A. Takaoka, et al., Nature 448 (7152), 501 (2007)). The best characterized of these responses involves activation of the TANK-binding kinase (TBK1)-

Interferon Regulatory Factor (IRF)-3 signaling axis to trigger transcriptional induction of IFN-alpha/beta genes (K. J. Ishii, et al., Nature 451 (7179), 725 (2008); K. A. Fitzgerald, et al., Nat Immunol 4 (5), 491 (2003); S. Sharma, et al., Science 300 (5622), 1148 (2003); K. J. Ishii, et al., Nat Immunol 7 (1), 40 (2006)). A second, less well-defined pathway leads to the activation of an 'inflammasome', which, via caspase-1, controls the catalytic cleavage of the pro-forms of the cytokines IL-1beta and IL-18 (D. A. Muruve, et al., Nature 452 (7183), 103 (2008); V. Hornung, et al., Nat Immunol 9 (8), 847 (2008)). Recently, a candidate receptor called DAI (DNA-dependent Activator of IFN-regulatory factors) was identified as an upstream component of the DNA induced IFN pathway (A. Takaoka, et al., Nature 448 (7152), 501 (2007)). Studies in cells lacking DAI suggest that additional receptors for cytoplasmic dsDNA-induced IFN responses exist (K. J. Ishii, et al., Nature 451 (7179), 725 (2008)). NLRP3, (also called Nalp3, Cryopyrin) has been shown to activate the caspase-1 pathway in response to internalized adenoviral DNA (D. A. Muruve, et al., Nature 452 (7183), 103 (2008)). Correspondingly, NLRP3- and ASC-deficient mice display reduced innate inflammatory responses to adenoviral particles. However, caspase-1 activation in response to transfected bacterial, viral, mammalian or synthetic DNA does not appear to involve NLRP3, although the adapter molecule ASC is involved in this response (D. A. Muruve, et al., Nature 452 (7183), 103 (2008); V. Hornung, et al., Nat Immunol 9 (8), 847 (2008)).

The innate immune system can also trigger the adaptive immune response by antigen-specific T and B lymphocytes. Before the development of adaptive immunity, natural killer cells play a decisive role in the innate immune defense against virus infected and malignant cells by virtue of their ability to recognize and destroy abnormal cells (H. R. Smith, et al., Proc. Natl. Acad. Sci. USA, 99:8826-8831 (2002); J. M. Moser, et al., Curr. Opin. Immunol., 14:509-516 (2002)). Innate immunity mediated by macrophages, neutrophils and natural killer (NK) cells is often the first line of host defense mechanism against microbial invasion. The innate immune system targets structurally conserved pathogen-associated molecular patterns (PAMPs) through specific germ-line encoded receptors called pattern recognition receptors (PRRs) (A. Aderem and R. J. Ulevitch, Nature, 406:782-787 (2000)).

Inflammasomes

"Inflammasomes" are protein complexes found in the cytosol that mediate the generation of proinflammatory cytokines, such as IL-33, IL-1beta and IL-18. The inflammasome can induce cell pyroptosis, a process of programmed cell death distinct from apoptosis. Inflammasomes contain a caspase enzyme, either caspase-1 or caspase-5, that processes procytokines into their active forms. Activity of the caspase enzyme component, and thus the production of pro-inflammatory cytokines, is often regulated. The assembly of an inflammasome complex is typically dependent on another component of the inflammasome. The exact composition of an inflammasome depends on the activator which initiates inflammasome assembly. For example, dsRNA will trigger assembly of one inflammasome complex variant whereas asbestos or other particulate matter will trigger assembly of a different variant. In some cases, a NOD-like receptor protein, such as NALP-3 modulates assembly of an inflammasome complex (F. Martinon, et al., Sem. Immunopathology 29:213 (2007)).

Inflammasome Assembly and Function

In some cases, an inflammasome is formed upon activation by a member of the NOD-LRR (nucleotide-binding oligomerization domain-leucine-rich repeat) protein family such as NALP1, NALP2, NALP3/Cryopyrin or Ipaf, and the adaptor protein, ASC, that has the ability to connect the NOD-LRR proteins with caspase-1 (J. Tschopp, et al., K. Nat Rev Mol Cell Biol 4:95-104 (2003)). Thus, receipt of an activating signal by NALP3 leads to the activation of caspase-1.

Muramyl dipeptide (MDP), a degradation product of the bacterial cell wall component peptidoglycans, and a contaminant of crude LPS, was recently shown to activate a NALP3 inflammasome (F. Martinon, et al. Curr Biol 14: 1929-34 (2004)) through NALP3's LRR domain, suggesting that NALPs, like Toll-like receptors (TLRs), are important for microbial detection (F. Martinon & J. Tschopp, Trends Immunol (2005)). In addition, inflammasomes are also proficient in sensing stress or endogenous "danger signals", such as extracellular ATP or hypotonic stress (F. Martinon, et al., J. Mol Cell 10:417-26. (2002); S. Mariathasan, et al., Nature 430:213-8 (2004)). ASC is required for LPS-induced activation of procaspase-1 independently of TLR-associated signal adaptor molecules (M. Yamamoto, et al., Genes Cells 9:1055-67 (2004)).

A NALP3 inflammasome is a conjugate of caspase-1, ASC and NALP3 and plays a role in the generation of IL-1beta. For example, macrophages from mice deficient in various components of the inflammasome, such as caspase-1, ASC and NALP3, are defective in IL-1 activation. Likewise, IL-1 receptor type I (IL-1R1) deficiency results in impaired neutrophil recruitment in NALP3-induced inflammation. Furthermore, inhibitors of the HSP90 chaperone inhibit the formation of the NALP3 inflammasome; these inhibitors also block IL-1 secretion by human monocytes and mouse macrophages, and inhibit neutrophil recruitment in mice (US20070161559A1, hereby incorporated by reference in its entirety).

As described in more detail herein, methods and compositions of the present invention encompass the discovery that certain inflammasome complexes contain an AIM2 polypeptide, ASC and caspase-1.

ASC

The adaptor protein "ASC" ("apoptosis-associated speck-like protein containing a CARD" ("caspase recruitment domain")) is a component of the inflammasome. In some inflammasome complexes, ASC binds to NALP3 via a pyrin domain (PYD) and recruits caspase-1 via a CARD domain. For NALP3-containing inflammasome complexes, ASC is involved in inflammasome assembly and also for caspase-1 activation and the conversion of IL-1beta (L. Ferrero-Miliani, et al., Clin. Exp. Immunol. 147:227-235 (2006); L. Bouchier-Hayes & S. Martin, EMBO Reports 3:616-621 (2002)). Alternative names for ASC in the art include PYCARD, CARDS, MGC10332, TMS1 and hASC.

As described in more detail herein, certain inflammasome complexes contain an AIM2 polypeptide, ASC and caspase-1.

Caspase-1

Caspases are a family of cysteine proteases that cleave proteins after aspartic acid residues. Caspases can be divided into two groups, the pro-apoptosis caspases and the proinflammatory caspases. The proinflammatory caspases include caspase-1 and caspase-5. These proteins generate inflammatory cytokines (e.g., IL-1beta, IL-6, IL-18, IL-33) by converting the precursor versions of these cytokines into their mature, active forms. Caspase-1 is localized primarily in monocytes and serves to convert precursor IL-1beta to the mature form (R. A. Black, et al., FEBS Lett., 247: 386-390 (1989); M. J. Kostura, et al., Proc. Natl. Acad. Sci. U.S.A., 86:5227-5231 (1989)). Enzymatically active caspase-1 has been previously described as a heterodimer composed of two subunits, p20 and p10 (20 kDa and 10 kDa molecular weight, respectively). These subunits are derived from a 45 kDa proenzyme (p45) by way of a p30 form, through an activation mechanism that is autocatalytic (N. A. Thornberry, et al., Nature, 356, pp. 768-774 (1992)). The caspase-1 proenzyme has been divided into several functional domains: a pro-domain (p14), a p22/20 subunit, a polypeptide linker and a p10 subunit. (N. A. Thornberry, et al., Nature, 356, pp. 768-774 (1992); Casano, et al., Genomics, 20, pp. 474-481 (1994)). Caspase-1 is also known in the art as apoptosis-related cysteine peptidase, IL-1beta converting enzyme (ICE) and IL-1beta convertase.

As described in more detail herein, certain inflammasome complexes contain an AIM2 polypeptide, ASC and caspase-1.

Interleukin 1-beta

"Interleukin 1" ("IL-1") is a major pro-inflammatory and immunoregulatory protein that stimulates fibroblast differentiation and proliferation, the production of prostaglandins, collagenase and phospholipase by synovial cells and chondrocytes, basophil and eosinophil degranulation and neutrophil activation (J. H. Oppenheim, et al., Immunology Today, 7, pp. 45-56 (1986)). IL-1 augments T-cell responses to mitogens (and indirectly activates B cells), increases expression of vascular adhesion molecules, and induces a number of other proinflammatory cytokines, chemokines, and inflammation-associated molecules that form an amplifying cascade to stimulate an immune response. The net effect of inducing these other immune stimulatory molecules is to recruit and activate macrophages, lymphocytes, and neutrophils to fight infection and to stimulate wound healing in response to tissue damage.

IL-1 is also involved in the pathogenesis of chronic and acute inflammatory and autoimmune diseases. For example, in rheumatoid arthritis, IL-1 is both a mediator of inflammatory symptoms and of the destruction of the cartilage proteoglycan in afflicted joints (D. D. Wood, et al., Arthritis Rheum. 26, 975, (1983); E. J. Pettipher, et al., Proc. Natl. Acad. Sci. USA 71, 295 (1986); W. P. Arend and J. M. Dayer, Arthritis Rheum. 38, 151 (1995)). IL-1 is also a highly potent bone resorption agent (J. J. Jandiski, J. Oral Path 17, 145 (1988); F. E. Dewhirst, et al., J. Immunol. 8, 2562 (1985)). It is alternately referred to as "osteoclast activating factor" in destructive bone diseases such as osteoarthritis and multiple myeloma (R. Bataille, et al., Int. J. Clin. Lab. Res. 21(4), 283 (1992)). In certain proliferative disorders, such as acute myelogenous leukemia and multiple myeloma, IL-1 can promote tumor cell growth and adhesion (M. R. Bath, J. Natl. Cancer Inst. 83, 123 (1991); F. Vidal-Vanaclocha, Cancer Res. 54, 2667 (1994)). In these disorders, IL-1 also stimulates production of other cytokines such as IL-6, which can modulate tumor development (Tartour, et al., Cancer Res. 54, p. 6243 (1994)). IL-1 is predominantly produced by peripheral blood monocytes as part of the inflammatory response and exists in two distinct agonist forms, IL-1a and IL-1P (B. S. Mosely, et al., Proc. Nut. Acad. Sci., 84, pp. 4572-4576 (1987); G. Lonnemann, et al., Eur. J. Immunol., 19, pp. 1531-1536 (1989)).

"IL-1beta", an endogenous pyrogen, is a highly inflammatory cytokine whose production and release into the extracellular environment is tightly controlled at least at three distinct steps (K. Burns, et al., J. Curr. Opin. Immunol. 15, 26-30 (2003)). The first step involves the production of the pro IL-1beta protein (p35) ("proIL-1beta"). The second step involves the cleavage of the precursor pro IL-1beta to produce the active IL-1beta protein (p17). This reaction can be the result of activation by a caspase-1 activating complex (F. Martinon, et al., Mol Cell 10, 417-26, (2002); S. Mariathasan, et al., Nature 430, 213-8 (2004)). In the third step, IL-1beta is released into the extracellular environment.

IL-1beta is a key mediator of inflammation and is required for an acute neutrophic inflammation response (e.g., the recruitment of neutrophils to the site of cell injury). For example, the IL-1beta receptor is required for MSU to mediate an inflammation response by the immune system in animals (but not for the initial production of IL-1beta by macrophages in response to MSU in vitro) (C. Chen, et al., J. Clin. Invest. 116:2262-2271 (2006); C. Chen, et al., Nature Med 13:851-856 (2007)). More specifically, and without wishing to be bound by any particular theory, it is believed that the initial production of IL-1beta by immune cells after exposure to cytosolic DNA can serve as the initiator of an inflammation response, which is then furthered by the release of additional IL-1 and other proinflammatory cytokines (e.g., the release of additional cytokines in response to the initial cytosolic DNA-induced IL-1beta production and release).

Conversion of pIL-1beta

IL-1beta is synthesized as a biologically inactive precursor, pIL-1beta, which lacks a conventional leader sequence and hence is not processed by a signal peptidase (C. J. March, Nature 3 15: 641-647 (1985)). Instead, pIL-1beta is cleaved by caspase-1 (originally known as "interleukin-1beta converting enzyme" ("ICE")) between Asp-116 and Ala-117 to produce the biologically active C-terminal fragment found in human serum and synovial fluid (P. R. Sleath, et al., J. Biol. Chem., 265:14526-14528 (1992); A. D. Howard, et al., J. Immunol., 147:2964-2969 (1991)). Processing by caspase-1 is also involved in the transport of mature IL-1beta through the cell membrane.

As described in more detail herein, certain inflammasome complexes comprising an AIM2 polypeptide, ASC and caspase-1 are involved in maturation of pro-IL-1beta.

AIM2 Polypeptide-Containing Inflammasomes

Certain methods and compositions of the present invention encompass the discovery that certain inflammasome complexes contain an AIM2 polypeptide, ASC, and caspase-1. Such AIM2 polypeptide-containing inflammasomes can mediate the generation of proinflammatory cytokine IL-1beta (see Examples 4 and 5).

AIM2, alternatively known as PISA, is a 343 amino acid polypeptide (see Genbank accession number AF024714.1; RefSeq accession number NP_004824.1). PISA/AIM2 is a member of the IFI20X/IFI16 family, and is known to expressed in the spleen, the small intestine, peripheral blood leukocytes, and the testis. PISA contains a PYD domain, which is involved in interaction with ASC (see e.g., Example 2), as well as a HIN200 domain that is involved in interaction with dsDNA (see e.g., Example 6). PISA/AIM2 plays a putative role in tumorigenic reversion and may control cell proliferation. Expression of PISA/AIM2 is induced by interferon-gamma.

Certain methods and compositions of the present invention also encompass the discovery that AIM2 polypeptides interact with ASC in the formation of a functional inflammasome. Without wishing to be bound by theory, it is believed that AIM2 polypeptides interact with ASC via a pyrin (PYD) domain (see Example 2). PYD domains are putative protein-protein interaction domains at the N-termini of several proteins thought to function in apoptotic and inflammatory signaling pathways (see Fairbrother, et al., Protein Science, 10:1911-1918 (2001)). PYRIN domains are predicted to be members of the six-helix bundle death domain-fold superfamily. This superfamily includes death domains (DDs), death effector domains (DEDs), and caspase recruitment domains (CARDs). Members of the death domain-fold superfamily are known to be mediators of protein-protein interactions found in many proteins involved in apoptosis and inflammation.

Additionally, certain methods and compositions of the present invention also encompass the discovery that AIM2 polypeptides interact with dsDNA in the formation of a functional inflammasome. Without wishing to be bound by theory, it is believed that an AIM2 polypeptide is able to bind dsDNA via a HIN200 domain (see Example 6).

Identification of Compounds that Modulate an AIM2 Polypeptide-Mediated Immune Response In certain embodiments, methods of identifying a compound that modulates an AIM2 polypeptide-mediated immune response are provided herein. For example, a cell that expresses an AIM2 polypeptide may be contacted with a test compound to generate a "test sample", which test sample is incubated under conditions and for a time sufficient for a cellular characteristic of an AIM2 polypeptide-mediated immune response to occur.

The term "AIM2 polypeptide" as used herein refers to a polypeptide that comprises the AIM2 amino acid sequence shown in RefSeq accession number NP_004824.1 or a variant polypeptide that is at least 70%, e.g., 75%, 80%, 85%, 90%, 95%, 96%, 97%, 98%, 99% or more, identical to the full length of the AIM2 amino acid sequence. AN AIM2 polypeptide will retain at least one function of the AIM2 amino acid sequence shown in RefSeq accession number NP_004824.1, including for example, the ability to interact with ASC, the ability to bind dsDNA, and/or the ability to form a caspase-1 activating inflammasome. In certain embodiments, an AIM2 polypeptide is a fusion polypeptide or a fluorescent fusion polypeptide. For example, an AIM2 polypeptide may be a fusion protein comprising a Yellow Fluorescent Protein (YFP), a Cyan Fluorescent Protein (CFP), Green Fluorescent Protein (GFP), Red Fluorescent Protein (RFP), or a fluorescent variant thereof. In some embodiments, the variants include substitutions only in regions not conserved among the family of PYHIN proteins (e.g., PYHIN1 (NM_198929.3), PYHIN2 (NM_005531.2), or PYHIN3 (NM_002432.1), which one of skill in the art can readily identify by aligning the sequence of the family members. In some embodiments, the variants include substitutions only in regions outside the PYD and/or HIN200 domains.

The term "cellular characteristic", when used in reference to an AIM2 polypeptide-mediated immune response, refers to a detectable phenotype exhibited by the cell when an AIM2 polypeptide-mediated immune response occurs. For example, a cellular characteristic of an AIM2 polypeptide-mediated immune response can include one or more of expression of NF-kappaB, type I IFN induction, cleavage of a pro-IL-1beta polypeptide, intracellular co-localization of the AIM2 polypeptide and an ASC polypeptide, and intracellular co-localization of the AIM2 polypeptide and a cytoplasmic dsDNA. Any detectable phenotype caused by an AIM2 polypeptide-mediated immune response is encompassed in the term "cellular characteristic of an AIM2 polypeptide-mediated immune response."

Methods known to those of ordinary skill in the art may be used to detect or measure a cellular characteristic of an AIM2 polypeptide-mediated immune response. For example, expression of NF-kappaB can be detected or measured by using a reporter construct containing regulatory elements known to be regulated by NF-kappaB. Such reporters include, without limitation, luciferase, Yellow Fluorescent Protein (YFP), a Cyan Fluorescent Protein (CFP), Green Fluorescent Protein (GFP), and Red Fluorescent Protein (RFP). In certain embodiments, a fluorescent variant of YFP, CFP, GFP, or RFP may be used as a reporter. For example, the polypeptide sequences of YFP, CFP, GFP, or RFP may contain one or more amino acid insertions, deletions or substitutions, so long as the variant still fluoresces. Such reporter constructs containing regulatory elements known to be regulated by NF-kappaB can be transfected into a cell of interest. The cell can then be subjected to a test compound, and expression of the reporter can be detected or measured.

Expression of NF-kappaB can also be detected or measured by techniques such as Western blotting, immunoprecipitation, dot blots, and the like. Moreover, expression of NF-kappaB can also be detected or measured by detecting or measuring the amount of NF-kappaB mRNA produced by a cell. Conventional techniques such as Northern blotting, PCR, quantitative PCR, real-time PCR, nuclease protection assays and the like may be used to detect or measure NF-kappaB mRNA.

In certain embodiments, a cellular characteristic to be detected or measured can be type I IFN induction. Such type I IFN induction can be detected or measured directly (e.g., by an antibody that recognizes type I IFN, Western blotting, immunoprecipitation, dot blotting, etc.) or indirectly. Without limitation, such indirect detection or measuring methods can include detecting or measuring the interaction of type I IFN with an IFN-alpha receptor and/or detecting or measuring a cellular response to IFN-alpha receptor activation by type I IFN binding.

In certain embodiments, a cellular characteristic to be detected or measured can be cleavage of a pro-IL-1beta polypeptide. Cleavage of a pro-IL-1beta polypeptide can be detected or measured by any of a variety of techniques known to those of ordinary skill in the art. For example, cleavage of a pro-IL-1beta polypeptide can be detected or measured by Western blot analysis, in which an uncleaved pro-IL-1beta polypeptide will result in a predominantly single band of a certain size, while a cleaved pro-IL-1beta polypeptide will predominantly result in two or more bands of smaller size. Additionally and/or alternatively, an antibody that recognizes one portion of the pro-IL-1beta polypeptide can be used to detect or measure cleavage of the pro-IL-1beta polypeptide.

Additionally or alternatively, cleavage of a pro-IL-1beta polypeptide can be detected or measured by use of an epitope tag. For example, a pro-IL-1beta polypeptide can be tagged with an epitope (e.g., at its N-terminus or its C-terminus) and expressed in a cell of interest. After subjecting the cell to a test compound, an antibody that recognized the epitope can be used to detect or measure cleavage of the epitope-tagged pro-IL-1beta polypeptide. Suitable epitopes include, without limitation, Flag, myc, T7, Glutathione-S-transferase, Yellow Fluorescent Protein (YFP), a Cyan Fluorescent Protein (CFP), Green Fluorescent Protein (GFP), Red Fluorescent Protein (RFP), and hemagglutinin. Those of ordinary skill in the art will be aware of additional suitable epitopes that can be used with one or more methods disclosed herein.

In certain embodiments, a cellular characteristic to be detected or measured can be intracellular co-localization of AIM2 and an ASC polypeptide or intracellular co-localization of AIM2 and a cytoplasmic dsDNA. Intracellular co-localization can be detected or measured by any of a variety of techniques known to those of ordinary skill in the art. For example, an AIM2 polypeptide, an ASC polypeptide, dsDNA or any combination thereof can be fluorescently labeled and introduced into a cell, and the localization of the fluorescently-labeled polypeptide or dsDNA can be detected or measured.

Useful fluorescent labels for AIM2 and ASC polypeptides include, without limitation, Yellow Fluorescent Protein (YFP), a Cyan Fluorescent Protein (CFP), Green Fluorescent Protein (GFP), and Red Fluorescent Protein (RFP). In certain embodiments, a fluorescent variant of YFP, CFP, GFP, or RFP may be used as a label. For example, the polypeptide sequences of YFP, CFP, GFP, or RFP may contain one or more amino acid insertions, deletions or substitutions, so long as the variant still fluoresces. In certain embodiments, an AIM2 polypeptide, an ASC polypeptide, or both can be fusion polypeptide comprising a fluorescent moiety. For example, an AIM2 polypeptide, an ASC polypeptide, or both can be fused in frame to YFP, CFP, GFP, or RFP or a variant thereof. The fusion polypeptide can comprise YFP, CFP, GFP, or RFP or a variant thereof at the N-terminus or the C-terminus, depending on the difficulty of cloning, the needs of the practitioner, etc.

Useful fluorescent labels for dsDNA include, without limitation, fluorescein, 6-FAM, TET, HEX, TAMRA, Texas Red, JOE, Cy5, Cy3, BODIPY FL, Oregon Green 488. Those of ordinary skill in the art are aware of other suitable labels. Those of ordinary skill in the art are also aware of suitable methods for labeling nucleic acids, and can apply such methods to labeling dsDNA for the purpose of practicing one or more methods provided herein. In certain embodiments, fluorescently labeled dsDNA is introduced (e.g., transfected) into a cell expressing an AIM2 polypeptide, an ASC polypeptide, or both.

Intracellular co-localization of an AIM2 polypeptide and an ASC polypeptide or intracellular co-localization of an AIM2 polypeptide and a cytoplasmic dsDNA, e.g., in the presence of a test compound, can be detected or measured by any of a variety of techniques. For example, fluorescently labeled polypeptides or dsDNA can be detected or measured by direct immunofluorescence (e.g., confocal microscopy of a fixed or immobilized cell). If two or more molecules suspected of co-localization each fluoresce at different wavelengths, each of the different wavelengths can be detected or measured, and the immunofluorescence results can be compared to determine whether the two or more molecules do in fact co-localize.

Additionally or alternatively, fluorescence resonance energy transfer (FRET) can be used to determine whether two or more molecules such as an AIM2 polypeptide and an ASC polypeptide co-localize intracellularly, e.g. in the presence of a test compound. FRET occurs when an excited donor fluorophore transfers its energy to an acceptor fluorophore in close proximity. Thus, if a first molecule and a second molecule are suspected of co-localization, the first molecule can be tagged with a first fluorescent label that upon excitation emits radiation of a given wavelength. If the second molecule is labeled with a second fluorescent label, which second fluorescent label is excited by the emission radiation of the first label, co-localization of the first and second molecules can be detected or measured by exciting the first molecule containing the first label, and detecting or measuring emission radiation of the second molecule containing the second label. In certain embodiments, the first and second labels are excited by different wavelengths. In such embodiments, excitation of the first label will be expected to have little or no direct effect on excitation of the second label. In certain embodiments, the excitation wavelengths of the first and second labels overlap. In such embodiments, excitation of the first label will also directly excite the second label to at least some extent. Thus, in detecting or measuring co-localization, the emission of the second label will need to be corrected for the additional excitation.

Additionally or alternatively, homogeneous time resolved fluorescence (HTRF) can be used to determine whether two or more molecules such as an AIM2 polypeptide and an ASC polypeptide co-localize intracellularly, e.g. in the presence of a test compound. HTRF employs FRET-like technology to detect and measure interaction of two or more molecules. A first antibody bearing a fluorescence donor and a second antibody bearing a fluorescence acceptor each recognize a separate molecule, which separate molecules are suspected of interacting (e.g., directly or indirectly). Once the first and second antibodies bind to their targets, interaction between the separate molecules is detected by fluorescence transfer of energy from the first antibody bearing a fluorescence donor to the fluorescence acceptor of the second antibody.

Additionally or alternatively, amplified luminescent-proximity homogeneous assay (e.g., AlphaScreen™) can be used to determine whether two or more molecules such as an AIM2 polypeptide and an ASC polypeptide co-localize intracellularly, e.g. in the presence of a test compound. An amplified luminescent-proximity homogeneous assay is a screening technology based on the transfer of energy from donor to acceptor microbeads brought together by a biomolecular interaction. Excitation of the donor beads converts ambient oxygen to singlet state oxygen, which can diffuse up to 200 nm. Provided a biomolecular interaction brings an acceptor bead in close proximity to the donor, the emitted singlet state oxygen induces a cascade of chemiluminescence in the acceptor bead, resulting in the emission of electromagnetic radiation of a defined wavelength or wavelength range, which can be detected or measured. In some embodiments, donor beads contain the photosensitizer phthalocyanine.

Additionally or alternatively, intracellular co-localization of AIM2 and an ASC polypeptide or intracellular co-localization of AIM2 and a cytoplasmic dsDNA can be detected or measured, e.g. in the presence of a test compound, by biochemical methods that test direct or indirect molecular interactions. For example, co-immunoprecipitation assays of cellular lysates can be performed. Co-immunoprecipitation of an AIM2 polypeptide and an ASC polypeptide, for example, strongly suggest that the two polypeptides bind each other either directly or indirectly. Thus, coimmunoprecipitation can be used to detect or measure whether a test compound modifies this interaction (e.g., by increasing or decreasing the binding). Additionally or alternatively, cellular lysates can be fractionated and the various fractions can be tested for the presence of an AIM2 polypeptide and an ASC polypeptide. ELISA type assays and DNA aptamer techniques are additional, non-limiting methods that can be used to detect or measure the extent to which an AIM2 polypeptide and an ASC polypeptide interact with each other in the presence of a test compound. Those of ordinary skill in the art will be aware of additional suitable biochemical methods that can be used to test direct or indirect molecular interactions, suggesting co-localization of the molecules of interest.

In certain embodiments, a test sample is incubated under conditions and for a time sufficient such that a cellular characteristic of an AIM2 polypeptide-mediated immune response would occur if a reference sample lacking the test compound were incubated under the same conditions and for the same time. A change in the detected cellular characteristic compared to a reference cellular characteristic that would be observed in a reference sample indicates that the test compound is a compound that modulates the AIM2-mediated immune response. In certain embodiments, a cellular characteristic of an AIM2 polypeptide-mediated immune response of a reference sample that lacks a test compound is observed. In certain embodiments, a cellular characteristic of an AIM2 polypeptide-mediated immune response of a reference sample that lacks a test compound is not observed. For example, a cellular characteristic of an AIM2 polypeptide-mediated immune response in a reference sample that lacks a test compound may be previously known.

For example, if a cellular characteristic such as expression of NF-kappaB, type I IFN induction, cleavage of a pro-IL-1beta polypeptide, intracellular co-localization of the AIM2 polypeptide and an ASC polypeptide, intracellular co-localization of the AIM2 polypeptide and a cytoplasmic dsDNA, or any combination thereof differs between a the cellular characteristic observed in a test sample that includes a test compound and the cellular characteristic that would be observed in a reference sample that lacks a test compound, such a difference indicates that the test compound modulates the AIM2-mediated immune response.

In certain embodiments, a difference in an observed cellular characteristic in a test sample that includes a test compound and a corresponding cellular characteristic that would be observed in a reference sample that lacks a test compound is qualitative. For example, a pro-IL-1beta polypeptide may be cleaved in the test sample, but may not be cleaved in the reference sample. Conversely, a pro-IL-1beta polypeptide may be cleaved in the reference sample, but may not be cleaved in the test sample. Similarly, an AIM2 polypeptide may co-localize with an ASC polypeptide, a dsDNA, or both in the test sample, but may not co-localize in the reference sample. Conversely, an AIM2 polypeptide may co-localize with an ASC polypeptide, a dsDNA, or both in the reference sample, but may not co-localize in the test sample. Additional qualitative differences can be detected or measured for other cellular characteristics of an AIM2 polypeptide-mediated immune response.

In certain embodiments, a difference in an observed cellular characteristic in a test sample that includes a test compound and a corresponding cellular characteristic that would be observed in a reference sample that lacks a test compound is quantitative. For example, a pro-IL-1beta polypeptide may be cleaved in the test sample, but may be cleaved to a reduced extent in the reference sample. Conversely, a pro-IL-1beta polypeptide may be cleaved in the reference sample, but may be cleaved to a reduced extent in the test sample. Cleavage of a pro-IL-1beta polypeptide may reduced by at least 5%, e.g., by at least 10%, 15%, 20%, 25%, 30%, 35%, 40%, 45%, 50%, 55%, 60%, 65%, 70%, 75%, 80%, 85%, 90%, 95%, 96%, 97%, 98%, 99%, or more in a reference sample as compared to a test sample, or vice versa. Similarly, an AIM2 polypeptide may co-localize with an ASC polypeptide, a dsDNA, or both in the test sample, but may co-localize to a reduced extent in the reference sample. Conversely, an AIM2 polypeptide may co-localize with an ASC polypeptide, a dsDNA, or both in the reference sample, but may co-localize to a reduced extent in the test sample. Co-localization of AN AIM2 polypeptide with an ASC polypeptide, a dsDNA, or both may be reduced to a level that is 95%, e.g., 90%, 85%, 80%, 75%, 70%, 65%, 60%, 55%, 50%, 45%, 40%, 35%, 30%, 25%, 20%, 15%, 10%, 5%, or less that seen in a test sample versus a reference sample, or vice versa. Additional quantitative differences can be detected or measured for other cellular characteristics of an AIM2 polypeptide-mediated immune response.

In certain embodiments, a nucleic acid encoding an AIM2 polypeptide is introduced into a cell, which nucleic acid is transcribed into an mRNA, which is then translated to produce the AIM2 polypeptide. For example, a vector comprising a nucleic acid encoding an AIM2 polypeptide may be transfected or transformed into a cell by any of a variety of techniques known to those of ordinary skill in the art. In certain embodiments, such a vector comprises a nucleic acid sequence that directs expression of an AIM2 polypeptide-encoding mRNA in a cell of interest, e.g. a promoter. In certain embodiments, a nucleic acid encoding an AIM2 fusion polypeptide is introduced into a cell, which AIM2 fusion polypeptide comprises an AIM2 polypeptide fused in frame to one or more additional polypeptides or polypeptide moieties. For example, an AIM2 fusion polypeptide may comprise an epitope tag such as, without limitation, Flag, myc, T7, Glutathione-S-transferase, Yellow Fluorescent Protein (YFP), a Cyan Fluorescent Protein (CFP), Green Fluorescent Protein (GFP), Red Fluorescent Protein (RFP), or hemagglutinin. In certain embodiments, a nucleic acid encoding an AIM2 fluorescent fusion polypeptide may be introduced into a cell. AN AIM2 fluorescent fusion polypeptide may comprise a polypeptide such as, without limitation, a Yellow Fluorescent Protein (YFP), a Cyan Fluorescent Protein (CFP), Green Fluorescent Protein (GFP), Red Fluorescent Protein (RFP), or a fluorescent variant thereof.

In certain embodiments, a nucleic acid encoding an ASC polypeptide is introduced into a cell, which nucleic acid is transcribed into an mRNA, which is then translated to produce the ASC polypeptide. For example, a vector comprising a nucleic acid encoding an ASC polypeptide may be transfected or transformed into a cell by any of a variety of techniques known to those of ordinary skill in the art. In certain embodiments, such a vector comprises a nucleic acid sequence that directs expression of an ASC polypeptide-encoding mRNA in a cell of interest, e.g. a promoter. In certain embodiments, a nucleic acid encoding an ASC fusion polypeptide is introduced into a cell, which ASC fusion polypeptide comprises an ASC polypeptide fused in frame to one or more additional polypeptides or polypeptide moieties. For example, an ASC fusion polypeptide may comprise an epitope tag such as, without limitation, Flag, myc, T7, Glutathione-S-transferase, Yellow Fluorescent Protein (YFP), a Cyan Fluorescent Protein (CFP), Green Fluorescent Protein (GFP), Red Fluorescent Protein (RFP), or hemagglutinin. In certain embodiments, a nucleic acid encoding an ASC fluorescent fusion polypeptide may be introduced into a cell. An ASC fluorescent fusion polypeptide may comprise a polypeptide such as, without limitation, a Yellow Fluorescent Protein (YFP), a Cyan Fluorescent Protein (CFP), Green Fluorescent Protein (GFP), Red Fluorescent Protein (RFP), or a fluorescent variant thereof.

In certain embodiments, a cell is stably transfected with a nucleic acid encoding an AIM2 polypeptide, an ASC polypeptide, or both. In certain embodiments, a cell is transiently transfected with a nucleic acid encoding an AIM2 polypeptide, an ASC polypeptide, or both.

Test Compounds

Test compounds to be used in methods described herein can be obtained using any method known in the art. For example, compounds can be obtained using any of the numerous approaches in combinatorial library methods known in the art, including: biological libraries; peptoid libraries (libraries of molecules having the functionalities of peptides, but with a novel, non-peptide backbone that are resistant to enzymatic degradation, but that nevertheless remain bioactive (e.g., Zuckermann et al., J. Med. Chem., 37:2678-2685 (1994)); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, Anticancer Drug Des. 12:145 (1997)).

Examples of methods for the synthesis of molecular libraries can be found in the art, for example in: DeWitt et al., Proc. Natl. Acad. Sci. U.S.A., 90:6909 (1993); Erb et al., Proc. Natl. Acad. Sci. U.S.A., 91:11422 (1994); Zuckermann et al., J. Med. Chem., 37:2678 (1994); Cho et al., Science, 261:1303 (1993); Carrell et al., Angew. Chem. Int. Ed. Engl., 33:2059 (1994); Carell et al., Angew. Chem. Int. Ed. Engl., 33:2061 (1994); and in Gallop et al., J. Med. Chem., 37:1233 (1994).

Libraries of compounds may be presented in solution (e.g., Houghten, Biotechniques, 13:412-421 (1992)), or on beads (Lam, Nature, 354:82-84 (1991)), chips (Fodor, Nature, 364: 555-556 (1993)), bacteria (Ladner, U.S. Pat. No. 5,223,409), spores (Ladner, U.S. Pat. No. 5,223,409), plasmids (Cull et al., Proc. Natl. Acad. Sci. U.S.A., 89:1865-1869 (1992)), or on phage (Scott and Smith, Science, 249:386-390 (1990); Devlin, Science, 249:404-406 (1990); Cwirla et al., Proc. Natl. Acad. Sci. U.S.A., 87:6378-6382 (1990); Felici, J. Mol. Biol., 222:301-310 (1991); Ladner supra.).

Antibodies can be used as test compounds. Such antibodies can be screened for their ability to inhibit or increase a cellular characteristic of an AIM2 polypeptide-mediated immune response. Antibody test compounds can be monoclonal antibodies. Methods of making such antibodies are known in the art.

Test compounds for modulation of an AIM2 polypeptide-mediated immune response include compounds that decrease the ability of a dsDNA to AIM2 polypeptide-mediated signaling. Such compounds can be, for example, poly(dA-dT) dsDNA.

Test compounds identified as candidate compounds that modulate an AIM2 polypeptide-mediated immune response can be considered candidate therapeutic compounds for the treatment of infections or disorders associated with an AIM2 polypeptide-mediated immune response including, without limitation, infection from bacterial or viral pathogens, systemic lupus erythematosus, rheumatoid arthritis and other autoimmune diseases.

In certain embodiments, a test compound acts as an antagonist to an AIM2 polypeptide-mediated immune response. Such test compounds will be useful, e.g., for decreasing an undesirable inflammatory response caused by activation of the innate immune system. In certain embodiments, a test compound acts as an agonist to an AIM2 polypeptide-mediated immune response. Such test compounds will be useful, e.g., for increasing a deficient inflammatory response of the innate immune system.

Cells

Any type of cell that can express an AIM2 polypeptide and/or ASC polypeptide can be used in methods described herein. In general, suitable cell types include cells of such as Chinese hamster ovary (CHO) cells available from the ATCC as CCL61, NIH Swiss mouse embryo cells NIH/3T3 (ATCC CRL 1658), HELA cells (ATCC CCL 2), baby hamster kidney cells (BHK), COS-7, COS-1, HEK293 (ATCC CRL 1573), Ltk-1, AV-12 (ATCC CRL 9595), and the like. Those of ordinary skill in the art will be aware of suitable cell lines, as well as methods of handling such cell lines such that they can be used in accordance with one or more methods disclosed herein.

Methods of Treating Disease or Infection

In certain embodiments, methods of treating a disease comprising administering to a patient or animal a compound that decreases expression of an AIM2 polypeptide are provided herein. As is shown in the present specification, decreasing expression of an AIM2 polypeptide resulted in an attenuation of poly(dA-dT)-mediated IL-1beta release, a cellular characteristic of AIM2 polypeptide-mediated immune response (see Example 5). Thus, in certain embodiments, decreasing expression of an AIM2 polypeptide can result in attenuation of an AIM2 polypeptide-mediated immune response. Attenuating an AIM2 polypeptide-mediated immune response is desirable when such an immune response results in detrimental effects on a patient or animal.

Any of a variety of diseases can be treated according to one or more methods disclosed herein. For example, certain autoimmune diseases have been associated with accumulation of accumulation of aberrant host DNA and exaggerated responses to such DNA (see e.g., K. J. Ishii and S. Akira, Trends in Immunology 27 (11), 525 (2006)). In certain embodiments, methods disclosed herein may be used to treat auto-immune diseases that include, but are not limited to, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing, loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis. For example, methods disclosed herein may be used to treat rheumatoid arthritis, systemic lupus erythematosus, scleroderma, dermatomyositis, or psoriasis. Any of a variety of other autoimmune diseases that are associated with accumulation of aberrant host DNA may be treated with methods disclosed herein.

In certain embodiments, methods of treating an infection comprising administering to a patient or animal a compound that decreases expression of an AIM2 polypeptide are provided herein. In certain embodiments, decreasing expression of an AIM2 polypeptide can result in attenuation of an AIM2 polypeptide-mediated immune response. Attenuating an AIM2 polypeptide-mediated immune response is desirable when such an immune response results in detrimental effects on a patient or animal.

In certain embodiments, a compound that decreases expression of an AIM2 polypeptide can be used to treat an infection caused by a bacterial pathogen. Non-limiting examples of bacterial pathogens that can be treated with method disclosed herein include the bacterial facultative and obligatory intracellular pathogens for example *Shigella* spp., *Francisella* spp. *Chlamyida* spp. *Listeria monocytogenes, Mycobacterium tuberculosis, Mycobacterium leprae, Mycobacterium avium intracellulare, Brucella* spp., *Salmonella* spp., *Legionella*, and *Rickettsia*. Those of ordinary skill in the art will be aware of other bacterial pathogens that can be treated by one or more methods disclosed herein.

In certain embodiments, a compound that decreases expression of an AIM2 polypeptide can be used to treat an infection caused by a viral pathogen. Non-limiting examples of viral pathogens that can be treated with method disclosed herein include viral pathogens of the following families: Adenoviridae, Picornaviridae, Herpesviridae, Hepadnaviridae, Flaviviridae, Retroviridae, Orthomyxoviridae, Paramyxoviridae, Papovaviridae, Rhabdoviridae and Togaviridae.

Those of ordinary skill in the art will be aware of other viral pathogens that can be treated by one or more methods disclosed herein.

In certain embodiments, methods of treating a disease provided herein comprise administering to a patient or animal an siRNA or an shRNA to decrease expression of an AIM2 polypeptide.

A small or short interfering RNA (an siRNA) is typically a 20-25 nucleotide-long double stranded RNA molecule that is a class of 20-25 nucleotide-long double-stranded RNA molecules that is involved in the RNA interference (RNAi) pathway. An siRNA interferes with the expression of a specific with which it shares nucleotide sequence identity or similarity. SiRNAs that are most effective in mammalian cells are duplexes composed or two complementary 21 nucleotide single-stranded RNAs that anneal to form a duplexed region of 19 basepairs and single-stranded overhangs of 2 nucleotides at their 3' ends. In some organisms (e.g., C. elegans, D. melanogaster and various plants) siRNAs can be created by the nucleolytic processing of longer dsRNAs. In mammalian cells they apparently can also be produced from short (e.g., less than 30 basepairs) hairpin RNAs, or shRNAs. At least in some organisms, SiRNAs are generated by an enzyme known as Dicer, which converts either long dsRNAs or small hairpin RNAs into siRNAs. The base-paired regions of siRNAs generally should correspond substantially, preferably exactly, to a "target sequence (e.g., a nucleic acid molecule encoding an AIM2 polypeptide).

In certain embodiments, methods of treating a disease comprising administering to a patient or animal an siRNA that decreases expression of an AIM2 polypeptide are provided herein. In some cases, expression of an AIM2 polypeptide is decreased by at least 25%, e.g., by at least 30%, 35%, 40%, 45%, 50%, 55%, 60%, 65%, 70%, 75%, 80%, 85%, 90%, 95%, 96%, 97%, 98%, 99%, or more upon administration of an siRNA directed to a nucleic acid molecule that encodes an AIM2 polypeptide. The siRNA can be administered by introducing a DNA that directs the in vivo transcription of an siRNA. Those of ordinary skill in the art will be aware of suitable DNA vectors for use in introducing an siRNA into a cell. Alternatively, an siRNA can be administered by introducing an RNA that has been synthesized in vitro. The introduced RNA can be a double-stranded siRNA, or a single-stranded hairpin RNA that is processed into an siRNA by RNases. RNAs that are synthesized in vitro can be synthesized either chemically, for example using phosphoramidite chemistry, or can be synthesized enzymatically, for example using an RNA polymerase and a DNA template containing an appropriate promoter sequence just upstream of the template sequence. The RNA can include modified nucleotides of any type, as well as other chemical modifications that impart characteristics such as improved stability, resistance to nucleases, greater efficacy, etc.

A small hairpin RNA or short hairpin RNA (shRNA) is a sequence of RNA that makes a tight hairpin turn that can be used to silence gene expression via RNA interference. shRNAs are single-stranded RNAs with regions of self-complementarity that can pair with one another, allowing the single strand to fold into an intramolecular duplex with a stem-loop type structure. Although the unpaired loop region can theoretically be any size, it is advantageous for the loop to be small enough to readily allow the self-complementary sequences within the same single-stranded RNA to find each other and form base pairs across their complementary region. In general, the sequence of the loop should not contain a palindromic sequence, nor should it be related to sequences adjacent to the target sequence, which is represented by one of the paired complementary regions, and to which the shRNA ultimately targets. Within the cell the loop of an shRNAs is thought to be cleaved and an intermolecular duplex, not unlike an siRNA, is formed. The stem region of the shRNA should generally contain approximately 19 base pairs, and generally the 3' end of the shRNA extending beyond the paired region is composed of multiple uracil residues. The base-paired regions of shRNAs should generally correspond substantially, preferably exactly, to a target sequence (e.g., a nucleic acid molecule encoding an AIM2 polypeptide).

In certain embodiments, methods of treating a disease comprising administering to a patient or animal an shRNA that decreases expression of an AIM2 polypeptide are provided herein. In some cases, expression of an AIM2 polypeptide is decreased by at least 25%, e.g., by at least 30%, 35%, 40%, 45%, 50%, 55%, 60%, 65%, 70%, 75%, 80%, 85%, 90%, 95%, 96%, 97%, 98%, 99%, or more upon administration of an siRNA directed to a nucleic acid molecule that encodes an AIM2 polypeptide. An shRNA can be administered by introducing a DNA that directs the in vivo transcription of an shRNA. Those of ordinary skill in the art will be aware of suitable DNA vectors for use in introducing an shRNA into a cell. Alternatively, an shRNA can be administered by introducing an RNA that has been synthesized in vitro. RNAs that are synthesized in vitro can be synthesized either chemically, for example using phosphoramidite chemistry, or can be synthesized enzymatically, for example using an RNA polymerase and a DNA template containing an appropriate promoter sequence just upstream of the template sequence. The RNA can include modified nucleotides of any type, as well as other chemical modifications that impart characteristics such as improved stability, resistance to nucleases, greater efficacy, etc.

Gene Therapy

Gene therapy is the insertion of genes into an individual's cells and tissues to treat a disease. In some cases, gene therapy can be used to treat a hereditary disease. Gene therapy typically aims to supplement a defective mutant allele with a functional one.

In general, one or more extra correct copies of genes are provided to complement the loss of function. A carrier called a vector is typically used to deliver the correct copy of the gene of interest to a patient's or animal's target cells. Currently, the most common types of vectors are engineered viruses that have been genetically altered to both be non-pathogenic and to carry normal human DNA.

Typically, target cells such as the patient's or animal's liver or lung cells are infected with the engineered viral vector that contains the correct copy of the gene of interest, along with a suitable regulatory region that can be used to direct expression of the gene of interest in the target cell. The engineered viral vector then delivers its genetic material, including the correct copy of the gene of interest, to the target cell. The correct copy of the gene of interest is integrated into the target cells genome, and expression directed by the regulatory region leads to the generation of a functional protein product, which restores the target cell to a normal state.

Various viral vectors can be used for gene therapy including, without limitation, retroviruses, herpes simplex viruses, adenoviruses, and adeno-associated viruses. Each of these viral vectors has natural host cell populations that they infect most efficiently. For example, retroviruses have limited natural host cell ranges. Although adenovirus and adeno-associated virus are able to infect a relatively broader range of cells efficiently, some cell types are refractory to infection by these viruses as well. Entry into potential host cells typically involves a favorable interaction between a protein on the surface of the virus and a protein on the surface of the cell. Several viral vectors have been developed in which the endogenous viral envelope proteins have been replaced by either envelope proteins from other viruses, or by chimeric proteins. Such viruses are referred to as pseudotyped viruses. For example, a common retroviral vector for use in gene therapy trials has been the lentivirus Simian immunodeficiency virus coated with the envelope proteins, G-protein, from Vesicular stomatitis virus. This vector is referred to as VSV G-pseudotyped lentivirus, and infects an almost universal set of cells.

A viral vector used to deliver a gene of interest to a target cell can trigger the innate immune response, decreasing the effectiveness of gene therapy. In certain embodiments, methods are provided herein that increase the effectiveness of gene therapy by suppressing the innate immune response to nucleic acids introduced into a cell. For example, methods of providing gene therapy to a patient or animal comprising administering to the patient or animal a gene therapy agent and a compound that decreases expression of an AIM2 polypeptide are provided herein. In certain embodiments, a gene therapy agent and a compound that decreases expression of an AIM2 polypeptide are administered simultaneously. Additionally or alternatively, in certain embodiments, a gene therapy agent and a compound that decreases expression of an AIM2 polypeptide are administered sequentially. For example, the innate immune response can be attenuated by administering a compound that decreases expression of an AIM2 polypeptide, after which a gene therapy agent may be administered.

A "gene therapy agent" as the term is used herein refers to an agent that is used to deliver a gene of interest to a target cell of a patient or animal. A gene therapy agent typically comprises a virus (e.g., is a retrovirus, an adenovirus, or an adeno-associated virus) that has been engineered to contain the gene of interest. A gene therapy agent will typically be engineered to contain a suitable regulatory region that can be used to direct expression of the gene of interest in the target cell.

In certain embodiments, methods of providing gene therapy to a patient or animal comprise administering to a patient or animal a gene therapy agent and an siRNA or an shRNA to decrease expression of an AIM2 polypeptide. In some cases, expression of an AIM2 polypeptide is decreased by at least 25%, 30%, 35%, 40%, 45%, 50%, 55%, 60%, 65%, 70%, 75%, 80%, 85%, 90%, 95%, 96%, 97%, 98%, 99%, or more upon administration of an siRNA or shRNA directed to a nucleic acid molecule that encodes an AIM2 polypeptide. An siRNA or an shRNA can be administered by introducing a DNA that directs the in vivo transcription of an siRNA or an shRNA. Those of ordinary skill in the art will be aware of suitable DNA vectors for use in introducing an siRNA or an shRNA into a cell. Alternatively, an siRNA or an shRNA can be administered by introducing an RNA that has been synthesized in vitro. RNAs that are synthesized in vitro can be synthesized either chemically, for example using phosphoramidite chemistry, or can be synthesized enzymatically, for example using an RNA polymerase and a DNA template containing an appropriate promoter sequence just upstream of the template sequence. The RNA can include modified nucleotides of any type, as well as other chemical modifications that impart characteristics such as improved stability, resistance to nucleases, greater efficacy, etc.

Improving Transfection Efficiency

In certain embodiments, methods of introducing a double-stranded DNA molecule into a cell having decreased AIM2 polypeptide expression are provided. For example, a double-stranded DNA molecule can be introduced into a cell by administering to the cell a compound that decreases expression of an AIM2 polypeptide, and contacting the cell with the double-stranded DNA molecule under transfection conditions such that the cell is transfected with the double-stranded DNA molecule. "Transfection conditions" refers to any condition or conditions under which a cell is able to take up foreign DNA. A variety of transfection conditions are known to those of ordinary skill in the art. Non-limiting examples include electroporation, heat shock, calcium phosphate-mediated transfection, liposomal transfection, lithium acetate-mediated transfection, and the like.

In certain embodiments, methods of introducing a double-stranded DNA molecule into a cell having a decreased AIM2 polypeptide expression comprise administering to a patient or animal a gene therapy agent and an siRNA or an shRNA to decrease expression of an AIM2 polypeptide. In some cases, expression of an AIM2 polypeptide is decreased by at least 25%, 30%, 35%, 40%, 45%, 50%, 55%, 60%, 65%, 70%, 75%, 80%, 85%, 90%, 95%, 96%, 97%, 98%, 99%, or more upon administration of an siRNA or shRNA directed to a nucleic acid molecule that encodes an AIM2 polypeptide. An siRNA or an shRNA can be administered by introducing a DNA that directs the in vivo transcription of an siRNA or an shRNA. Those of ordinary skill in the art will be aware of suitable DNA vectors for use in introducing an siRNA or an shRNA into a cell. Alternatively, an siRNA or an shRNA can be administered by introducing an RNA that has been synthesized in vitro. RNAs that are synthesized in vitro can be synthesized either chemically, for example using phosphoramidite chemistry, or can be synthesized enzymatically, for example using an RNA polymerase and a DNA template containing an appropriate promoter sequence just upstream of the template sequence. The RNA can include modified nucleotides of any type, as well as other chemical modifications that impart characteristics such as improved stability, resistance to nucleases, greater efficacy, etc.

In certain embodiments, a cell into which a double-stranded DNA molecule is introduced is a mammalian cell. As is known to those of ordinary skill in the art, certain mammalian cell are resistant to transfection with foreign DNA. Such cells, include, for example, immune cells such as dendritic cells and monocytes. In certain embodiments, a cell into which a double-stranded DNA molecule is introduced is a dendritic cell. In certain embodiments, a cell into which a double-stranded DNA molecule is introduced is a monocyte. Other cell types that are resistant to transfection with foreign DNA will be known to those of ordinary skill in the art, and methods disclosed herein can be used to improve transfection efficiency when introducing foreign DNA into such cell types.

In certain embodiments, cells having decreased AIM2 polypeptide expression that are transfected with a double-stranded DNA may be introduced into a subject for therapeutic purposes. For example, dendritic cells, monocytes, or other cells may be transfected with a double-stranded DNA molecule having a portion that encodes a therapeutically beneficial polypeptide. Such transfected cells may then be introduced into a subject, such that the therapeutically beneficial polypeptide functions in the subject.

Increasing Cellular Response to dsDNA

In certain embodiments, a cell's innate immune response to a dsDNA is increased by introducing into the cell a nucleic acid molecule comprising a nucleic acid sequence that encodes an AIM2 polypeptide. For example, a vector comprising a nucleic acid encoding an AIM2 polypeptide may be introduced into a cell by any of a variety of techniques known to those of ordinary skill in the art (e.g., transfection, transformation). In certain embodiments, a nucleic acid molecule comprising an AIM2 polypeptide-encoding nucleic acid sequence additionally comprises a control nucleic acid sequence that directs expression of the AIM2 polypeptide-encoding nucleic acid sequence in the cell. For example, those of ordinary skill in the art will be aware of a variety of suitable promoters or other control elements that can be used to direct expression of the AIM2 polypeptide-encoding nucleic acid sequence in a cell of interest. In certain embodiments, a control nucleic acid sequence is constitutive such that the AIM2 polypeptide will be expressed in a generally continuous manner. In certain embodiments, a control nucleic acid sequence is inducible such that the AIM2 polypeptide will be expressed only in response to certain stimuli. Such inducing stimuli may be controlled by the practitioner.

Cells having an increased innate immune response to dsDNA are useful for any of a variety of purposes. For example, such cells can be used as research tools to screen for test compounds that modulate an AIM2 polypeptide-mediated immune response. For example, by modulating the level of the innate immune response, a researcher can more precisely control experimental conditions comprising the use of test compounds and/or may gain data or insight into a mechanism of the innate immune response that could not be otherwise gained. Additionally or alternatively, cells having an increased innate immune response may be used to study the pathogenesis of infection. As such, methods of generating cells having an increased innate immune response have great utility to those of ordinary skill in the art.

In certain embodiments, methods of increasing a cell's innate immune response to a dsDNA are used to treat a patient or animal suffering from an infection such as, without limitation, a bacterial or a viral infection. In certain embodiments, a patient's or animal's innate immune response is increased by introducing into one or more cells of the patient or animal a nucleic acid molecule comprising a nucleic acid sequence that encodes an AIM2 polypeptide. Additionally or alternatively, a patient's or animal's innate immune response is increased by introducing into one or more cells of the patient or animal a compound that increases expression or activity of an AIM2 polypeptide. Such methods are useful, for example, when a patient's or animal's endogenous innate immune response is deficient, for example as a result of genetic or epigenetic events. Any of a variety of methods can be used to introduce a nucleic acid molecule comprising a nucleic acid sequence that encodes an AIM2 polypeptide into a patient or animal such as, without limitation, viral delivery, delivery of naked DNA, delivery via lipoplexes or polyplexes, etc.

In certain embodiments, methods of increasing a cell's innate immune response to a dsDNA are used to improve the effectiveness of vaccination. As is known to those of ordinary skill in the art, a genetically engineered vaccinia virus can be used to vaccinate an animal or a patient against a specific antigen. Antigens delivered via an engineered vaccinia virus often exhibit increased immunogenicity due to the adjuvant properties of the vaccinia virus itself. In certain embodiments, the effectiveness of such an immunization is increased by introducing into one or more cells of the patient or animal a nucleic acid molecule comprising a nucleic acid sequence that encodes an AIM2 polypeptide. Additionally or alternatively, the effectiveness of an immunization is increased by introducing into one or more cells of the patient or animal a compound that increases expression or activity of an AIM2 polypeptide. In certain embodiments, expression and/or activity of an AIM2 polypeptide are increased by 20%, e.g., by 30%, 40%, 50%, 60%, 70%, 80%, 90%, 100%, 150%, 200%, 250%, 300%, 400%, 500% or more. Methods and compositions to increase the expression or activity of an AIM2 polypeptide as described herein may be used to increase the effectiveness of vaccination against any of a variety of antigens, such as, for example, antigens to bacteria and viruses.

In certain embodiments, a nucleic acid molecule that encodes an AIM2 polypeptide is introduced into a cell in vitro. In certain embodiments, a nucleic acid molecule that encodes an AIM2 polypeptide is introduced into a cell in vivo.

Certain embodiments of methods and compositions provided herein are further illustrated by the following examples. The examples are provided for illustrative purposes only. They are not to be construed as limiting the scope or content of the invention in any way.

EXAMPLES

Example 1

Methods and Reagents

Plasmid constructs: Full length human AIM2 (AS 1-356; based on BC010940.1), AIM2-PYD (1-83), AIM2-HIN (148-356), PYHIN1 (1-461; based on NM_198929), PYHIN1-PYD (1-84), PYHIN2 (1-729; based on NM_005531), PYHIN2-PYD (1-84), PYHIN3-PYD (1-84; based on NM_002432) and NLRP3-PYD (1-87; based on NM_004895.3) were cloned by PCR from cDNA into pEF-BOS-C-term-CFP by using PCR-generated XhoI and BamHI restriction sites. AIM2 full length, AIM2-PYD and AIM2-HIN were subcloned into pEFBOS-C-term-FLAG/HIS using XhoI and BamHI. Murine pro-IL-1beta (1-269) was obtained by PCR from cDNA and fused into pEFBOS-C-term-GLuc/FLAG using XhoI and BglII/BamHI. All constructs obtained by PCR-cloning were confirmed by sequencing. Expression plasmids (pCI) encoding human Caspase-1 and ASC-HA were from Millennium Pharmaceuticals (Cambridge, Mass.).

Reagents: ATP, LPS, poly(deoxyadenylic-thymidylic) acid sodium salt poly(dA-dT), were purchased from Sigma-Aldrich. A555-conjugated choleratoxin B was obtained from Molecular Probes, Invitrogen. DRAQ5 was purchased from Biostatus. Vaccinia virus (Western Reserve strain) was kindly provided by Drs. Lianjun Shen and Kenneth Rock (University of Massachusetts Medical School, Worcester, Mass.). Anthrax lethal toxin was from List Biologicals (5 ug/ml PA and 5 ug/ml LF).

All cDNAs were cloned by PCR from cDNA into pEF-BOS-C-term-CFP and subcloned into pEFBOS-C-term-FLAG/HIS as indicated. Biotinylated and FITC-labeled poly (dA-dT) were made by adding Biotin-dUTP or FITC-dUTP (Fermentas) in a molar ratio of 1:8 to dTTP in the enzymatic synthesis of poly(dA-dT) as described (H. K. Schachman, et al., The Journal of Biological Chemistry 235, 3242 (1960)).

Mice: NLRP3 and ASC-deficient mice (NLRP3−/− and Pycard−/− respectively) were as previously described (T. D. Kanneganti, et al., Nature 440 (7081), 233 (2006)). Both strains, as well as NLRP6−/− and NLRP12−/− mice were kindly provided by Millennium Pharmaceuticals (Cambridge, Mass.). Caspase-1-deficient mice were from R. Flavell (Yale University, New Haven, Conn.). C57BL/6 mice, 129/Sv mice, C57/B16×129 F1 mice, IL-1R-deficient (Il1r1−/−) were purchased from Jackson Laboratories (Bar Harbor, Me.). Seven to nine week-old animals were used in all experiments. All mouse strains were bred and maintained under specific pathogen-free conditions in the animal facilities at the University of Massachusetts Medical School.

Bioinformatics: Pyrin domain containing sequences were retrieved from UniProt after identifying them in SMART. A multiple sequence alignment of selected pyrin domains was generated using MUSCLE (R. C. Edgar, Nucleic acids research 32 (5), 1792 (2004)). Secondary structure elements from the POP1 crystal structure (A. Natarajan, et al., The Journal of Biological Chemistry 281 (42), 31863 (2006); PDB code: 2HM2) were mapped to the multiple sequence alignment in PFAAT (D. R. Caffrey, et al., BMC Bioinformatics 8, 381 (2007)). Prediction of nuclear targeting sequences and subcellular localization was done using PSORTII (psort.ims.u-tokyo.ac.jp/).

Cell culture and stimulation: Bone marrow derived macrophages were generated as described (M. Severa, et al., The Journal of Biological Chemistry 281 (36), 26188 (2006)). Macrophages were stimulated at a cell density of $2\times10^6$ cells/ml. All primary cells and cell lines were cultured in DMEM supplemented with L-glutamine, ciprofloxacin (Cellgro) and 10% fetal calf serum (Hyclone). All experiments that were performed for caspase-1 immunoblot analysis were carried out in serum free DMEM medium. ATP stimulations were carried out at 5 mM one hour prior to harvesting supernatants. Poly(dA-dT) DNA was transfected using Lipofectamine 2000 at a concentration of 1 μg/ml according to the manufacturer's instructions. Expression plasmids were transfected into 293T cells using GeneJuice (Novagen) according to the manufacturer's instructions.

ELISA: Cell culture supernatants were assayed for IL-1beta using ELISA kits from BDBiosciences (Franklin Lakes, N.J.) according to the manufacturer's instructions. To measure intracellular IL-1beta, cells were washed and subjected to three freeze thaw cycles in assay diluent.

Confocal microscopy: Confocal microscopy was performed on a Leica SP2 AOBS confocal laser scanning microscope. Separation of CFP and YFP was performed using sequential scanning and 405 and 514 nm excitation.

Flow cytometry Fluorescence Resonance Energy Transfer (FRET): FRET is a dipole-dipole interaction where an excited donor fluorophore transfers its energy to an acceptor fluorophore in close proximity (1-10 nm). Shortly, three fluorescent intensities were measured: I1—direct excitation and emission of donor, I2—indirect excitation and direct emission of acceptor (also called sensitized emission), and I3—direct excitation and emission of acceptor. After full correction for spectral bleed-through and cross excitation, FRET efficiency is calculated on a cell-by-cell basis (G. Szentesi, et al., Computer Methods and Programs in Biomedicine 75 (3), 201 (2004)) and then calculated FRET efficiency histograms were plotted with GraphPad Prism 5.01 (GraphPad Software).

Immunoblot analysis: For immunoblotting, cells were lysed in lysis buffer (150 mM NaCl, 10 mM Tris HCl pH 7.4, 1% CHAPS, protease inhibitor cocktail (Roche Applied Science)) and separated on sodium dodecyl sulphate-polyacrylamide gels and then transferred to nitrocellulose membranes (Amersham). For caspase-1 immunoblotting, supernatants were precipitated as previously described (V. Hornung, et al., Nat Immunol 9 (8), 847 (2008)). Membranes were blocked with 5% milk proteins in PBS and 0.05% Tween-20 and then incubated with the following antibodies: Anti murine caspase-1 p10 (sc-514, Santa Cruz Biotechnology), anti FLAG (M2, Sigma), anti HA (Roche Applied Science) or anti CFP (Santa Cruz Biotechnology). Species specific HRP-conjugated secondary antibodies were used and proteins detected using ECL reagent (GE Healthcare).

Co-immunoprecipitation assays: 293T cells in 24 wells were transfected with 1550 ng of the PYD-CFP expression plasmid of interest and 50 ng of ASC-HA. 24 h after transfection, cells were lysed with lysis buffer. Lysates were cleared by centrifugation at 20,000 g for 30 minutes and subsequently incubated with anti-HA agarose beads for 2 h at 4° C. Beads were washed 5 times and then boiled with Laemmli buffer for immunoblot analysis. THP1 cells were differentiated with PMA and primed with sendai virus (300 HAU/ml) overnight and subsequently lysed in high salt lysis buffer (250 mM NaCl, 10 mM Tris HCl pH 7.4, 1% CHAPS, protease inhibitor cocktail). Lysates were cleared by centrifugation at 20.000 g for 30 min, the salt concentration was adjusted to 125 mM NaCl and ASC was immunoprecipitated using polyclonal rabbit anti-ASC (Alexis, AL177) bound to protein G sepharose overnight. After 6 washes, beads were boiled with Laemmli buffer for immunoblot analysis.

Quantitative real-time PCR: RNA from murine macrophages was extracted with the RNeasy kit (Qiagen Inc., Valencia, Calif.). cDNA was synthesized with the iScript cDNA synthesis kit (Biorad, Hercules, Calif.), and quantitative RT-PCR analysis was performed on a DNA engine Opticon 2 cycler (MJ Research, Watertown Mass.) with the iQ SYBR Green Supermix (Biorad, Hercules, Calif.). The specificity of amplification was assessed for each sample by melting curve analysis. Relative quantification was performed using standard curve analysis. The murine quantification data are presented as a ratio to the hypoxanthine phosphoribosyltransferase 1 (HPRT1) level. The following primers for detection of IFN-beta, HPRT1 mRNAs were used:

```
mmHPRT1 Forward
(5'-CTGGTGAAAAGGACCTCTCG-3'[SEQ ID NO: 1])
and mmHPRT1 Reverse
(5'-TGAAGTACTCATTATAGTCAAGGGCA-3'[SEQ ID NO: 2]);

mmIFN-beta Forward
(5'-ATAAGCAGCTCCAGCTCCAA-3'[SEQ ID NO: 3])
and
mmIFN-beta Reverse
(5'-CTGTCTGCTGGTGGAGTTCA-3'[SEQ ID NO: 4]);

mmAIM2 Forward
(5'-GGCCGCATAGTCATCCTTTA-3'[SEQ ID NO: 5])
and mmAIM2 Reverse
(5'-CAACAGCATTTCCCGGTACT-3'[SEQ ID NO: 6]);
and mmNLRP3 Forward
(5'-ATGCTGCTTCGACATCTCCT-3'[SEQ ID NO: 7])
and mmNLRP3 Reverse
(5'-AACCAATGCGAGATCCTGAC-3'[SEQ ID NO: 8]).
``` shRNA mediated silencing: The lentiviral shRNA expression plasmids were purchased from OpenBiosystems (Huntsville, Ala.). The shRNAs targeting AIM2 are TRCN0000096104 (#1), TRCN0000096105 (#2), TRCN0000096106 (#3). The control shRNA is directed against murine IFIH1 (TRCN0000103648) and was confirmed not to have impact on NLRP3 expression and AIM2 expression. The production of viral particles and transduction of target cells were conducted according to the following protocols (see www.broad.mit.edu/genome_bio/trc/publicProtocols.html).

AlphaScreen Assay: The AlphaScreen (amplified luminescent-proximity homogeneous assay) was set up as an association assay. The protein of interest was transiently expressed in 293T cells and purified using FLAG beads (Sigma) binding to the C-terminal FLAG/HIS tag. The protein of interest was incubated at a concentration of 100 nM with biotinylated ligand at the indicated concentration in PBS, 0.1% BSA, and 0.01% Tween 20 for 60 min. Subsequently, Nickel chelate acceptor beads (binding to the HIS tag) and streptavidin-coated donor beads (Alphascreen beads, Perkin Elmer) were added from 5× stock concentrations. After 30 minutes incubation at 25° C. in the dark, samples in white 384-well plates (Proxiplate, Perkin Elmer) were read with the Envision HT microplate reader (Perkin Elmer). Data were analyzed by GraphPad Prism.

Reporter assays: For reporter assays, 293T cells (2×10E4 cells/100 μl/well in 96-well plates) were transfected with 50 ng of the indicated luciferase reporter gene. The thymidine kinase Renilla-luciferase reporter gene (Promega) (50 ng/well) was co transfected in order that the data could be normalized for transfection efficiency. In all cases, cell lysates were prepared and reporter gene activity was measured using the Dual Luciferase Assay System (Promega). Data are expressed as the mean relative stimulation+S.D. All of the experiments described were performed a minimum of three occasions and gave similar results.

siRNA transfection: THP1 cells were differentiated for 3 h using 0.5 μM PMA. Subsequently cells were plated at 2.5×10E4 cells/100 μl/well in 96-well plates and transfected with siRNA targeting human AIM2 (sense strand: 5'-CCCGAA-GATCAACACGCTTCA-3' [SEQ ID NO: 9]), human ASC (sense strand: 5'-CGGGAAGGTCCTGACGGATGA-3' [SEQ ID NO: 10]) or human TLR8 (5'-GGGAG-UUACUGCUUGAAGA-3' [SEQ ID NO: 11]) using 275 ng siRNA and 0.75 μl Lipofectamine 2000. 48 h after transfection cells were stimulated as indicated.

Cell viability assay: To quantify cell viability, macrophages (1×10E5 cells/100 μl/well in 96-well plates) were treated as described and subsequently incubated for 24 h. After 24 h, cells were washed with PBS and incubated in PBS with 5 μM calcein AM (Invitrogen) for 30 min at 37° C. The number of viable cells was assessed by counting fluorescent cells in two independent visual fields (20×) using ImageJ or by determining the overall fluorescence intensity using an Envision HT microplate reader.

Example 2

Identification of AIM2

Figure 5:
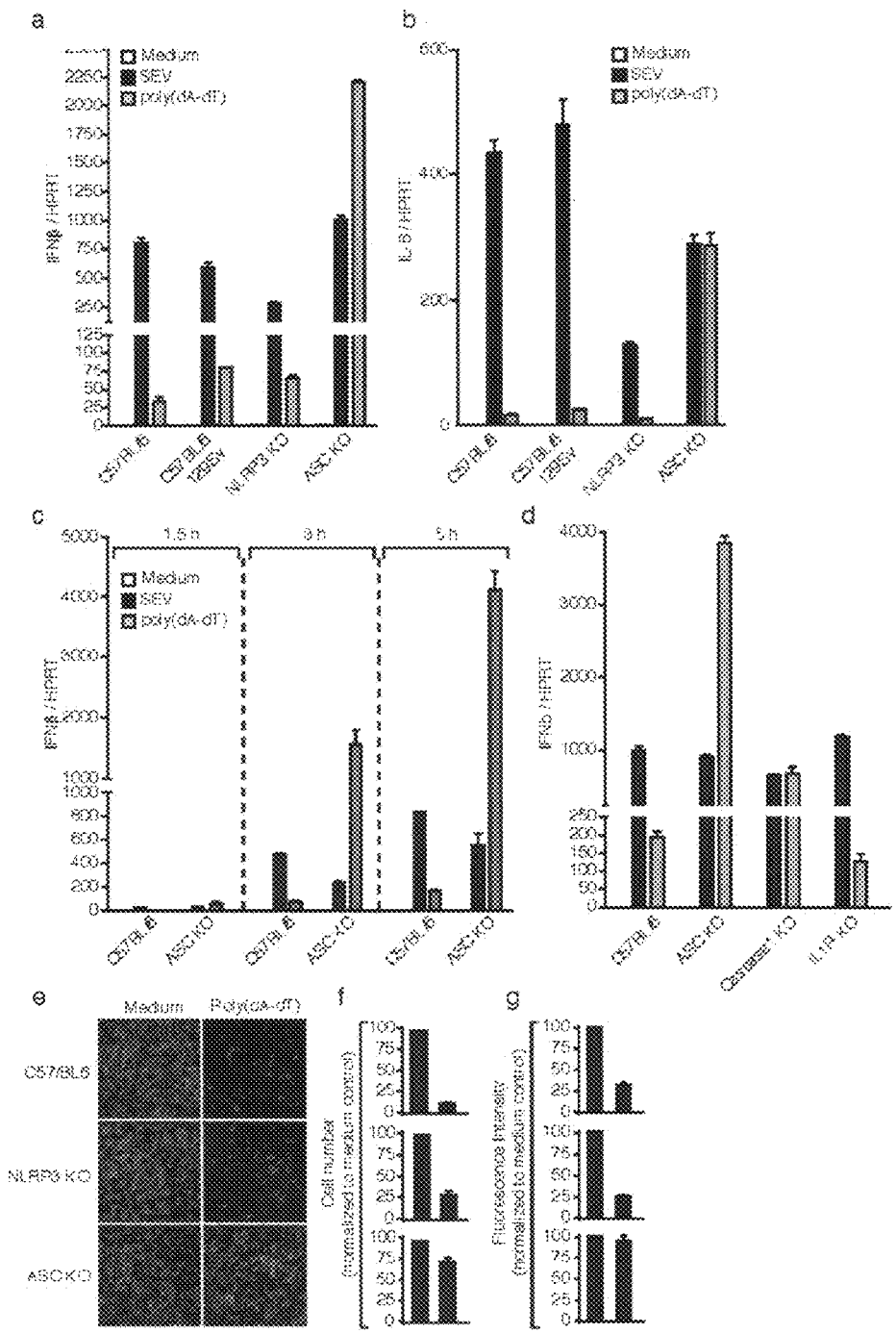
FIG. 5 shows that ASC-deficient macrophages are resistant to dsDNA-triggered cell death and show increased cytokine production in response to cytosolic dsDNA. a and b) Macrophages from either wild type, ASC- or NLRP3-deficient mice were transfected with poly(dA-dT) or stimulated with Sendai virus (300 HAU/ml). After 5 h, IFN-beta, IL-6 and HPRT1 mRNA expression was determined by real time PCR, whereas IFN-beta (a) or IL-6 (b) expression levels were normalized to HPRT1 expression. c) Macrophages from wild type or ASC-deficient mice were treated as in (a) and IFN-β/HPRT1 expression was determined 1.5, 3 and 5 h after stimulation. d) Macrophages from either wild type, ASC-caspase-1- or IL1R deficient mice were treated as in (a) and IFN-β/HPRT1 expression was determined 5 h after stimulation. e) Macrophages were transfected with poly(dA-dT) or left untreated. 24 h after transfection viable cells were labeled using calcein AM and subsequently visualized using fluorescent microscopy. Viable cells were counted in two independent visual fields of a 20× objective using ImageJ (panel f). In addition, overall fluorescent intensity was assessed (panel g). One representative experiment out of two independent experiments (panels a, b, c, d, e and f) is depicted as mean values±s.d.

Synthetic B-form double stranded DNA, poly(dA-dT)•poly(dA-dT) [hereafter referred to as poly(dA-dT)]) was used as a model ligand to study DNA signaling (K. J. Ishii, et al., Nat Immunol 7 (1), 40 (2006)). In addition to NLRP3 (G. A. Manji, et al., The Journal of Biological Chemistry 277 (13), 11570 (2002)), the related proteins NLRP6 (J. M. Grenier, et al., FEBS Lett 530 (1-3), 73 (2002)) and NLRP12 (L. Wang, et al., The Journal of Biological Chemistry 277 (33), 29874 (2002)) have previously been shown to associate and function upstream of ASC. The role of these NLRs in dsDNA-mediated inflammasome activation was tested using bone marrow derived macrophages from mice lacking these NLRs. While ASC deficient macrophages failed to activate caspase-1 and trigger IL-1beta release in response to poly (dA-dT), macrophages lacking NLRP3, -6 and -12 responded normally (FIG. 1a). Surprisingly, when IFN-beta production was monitored, it was found that macrophages lacking ASC had a greatly enhanced poly(dA-dT)-induced IFN-beta response, which was not observed in cells lacking NLRP3, the IL1R or to a lesser extent caspase-1 (FIG. 5).

The PFAM database was searched and several PYD-domain containing proteins were identified, which proteins also contained HIN200 domains. The HIN200 domain has previously been shown to function as a DNA binding domain (M. Albrecht, et al., Biochem Biophys Res Commun 327 (3), 679 (2005)). In humans, the HIN200 protein family consists of four members (S. Landolfo, et al., Biochimie 80 (8-9), 721 (1998)); PYHIN1 (IFIX) (Y. Ding, et al., Oncogene 23 (26), 4556 (2004); NCBI Reference Sequences: NM_152501.3, NM_198929.3, NM_198928.3, and NM_198930.2), PYHIN2 (IFI16) (J. A. Trapani, et al., Immunogenetics 36 (6), 369 (1992); NCBI Reference Sequence: NM_005531.2), PYHIN3 (MNDA) (G. R. Burrus, et al., Journal of Cellular Biochemistry 48 (2), 190 (1992); NCBI Reference Sequence: NM_002432.1) and PYHIN4 (see AIM2 (K. L. DeYoung, et al., Oncogene 15 (4), 453 (1997); Genbank accession number AF024714.1; RefSeq accession number NP_004824.1; NCBI Reference Sequence: NM_004833.1), also referred to as PISA for PYHIN Protein Stimulating ASC), each of which is encoded on the same locus on chromosome 1 (L. E. Ludlow, et al., Exp Cell Res 308 (1), 1 (2005)). A multiple sequence alignment of PYD domains from the PYHIN family with selected PYD domains from the NLRs is shown in FIG. 1b. Sequence analysis of PYHIN 1-3 predicted that these proteins would localize to the nucleus (FIG. 1c, lower panel). In contrast, AIM2 was predicted to reside in the cytosolic compartment. The subcellular localization of these proteins was directly examined using fluorescent protein chimeras and their subcellular localization was analyzed by confocal microscopy. Consistent with the predicted localizations, PYHINS 1-3 predominantly localized to the nucleus, while AIM2 was almost exclusively cytoplasmic (FIG. 1d).

Figure 2:
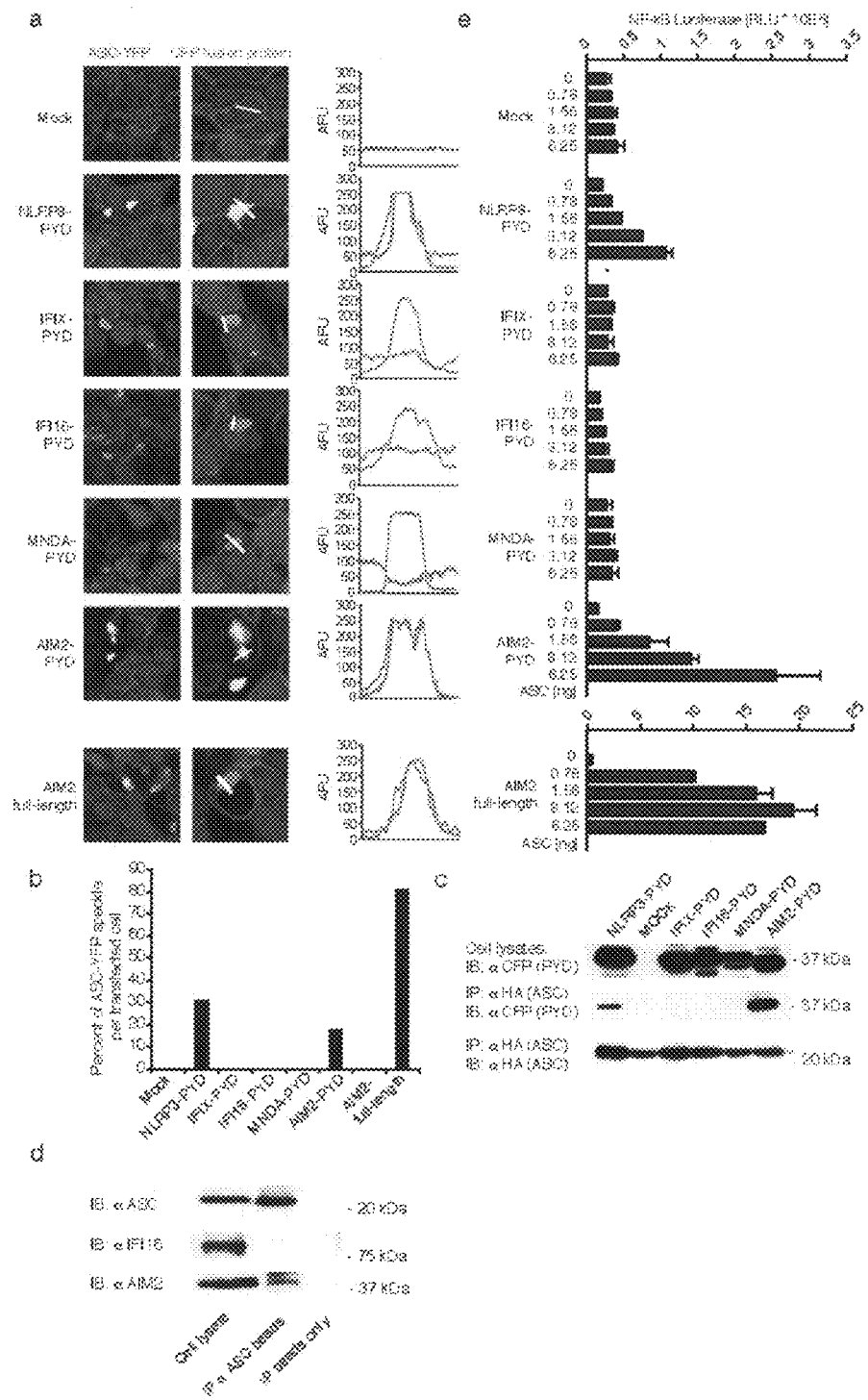
FIG. 2 shows that the PYD domain of AIM2 interacts with ASC. a) Stable HEK293-ASC-YFP (shown in green in the original) cells were transiently transfected with CFP-tagged PYD domains of NLRP3, PYHIN-1, PYHIN-2, PYHIN-3 or AIM2 or with CFP-tagged full-length AIM2 (all in red in the original), the membrane was stained with choleratoxin (shown in blue in the original) and cells were then imaged by confocal microscopy. Fluorescence intensities of the green (YFP-ASC) and red (PYD-CFP) channels were quantified along selected lines (white lines) and the percentage of ASC-YFP speckles per transfected cells assessed (panel b). c) 293T cells were transfected with expression plasmids encoding HAtagged ASC and CFP-tagged constructs as in panel a. The protein levels of the CFP-tagged PYD proteins in cell lysates were assessed by immunoblot analysis (INPUT, upper panels). Cell extracts were immunoprecipitated (IP) with anti-HA antibodies and immunoblotted (WB) with anti-HA antibody and anti-CFP antibody (lower panel). d) ASC was immunoprecipitated from THP-1 cell lysates primed with Sendai virus, whereas beads without anti-ASC antibody served as a negative control. The presence of ASC, PYHIN-2 and AIM2 was assessed by immunoblot analysis in the cell lysate and the ASC immunoprecipitation. The band above the AIM2 band in the ASC immunoprecipitation corresponds to the heavy chain of the anti-ASC antibody that is also detected by the secondary antibody. E) 293T cells were transfected with a multimerized NF-"B luciferase reporter construct together with fixed amounts of constructs as in (a) alone or together with increasing amounts of ASC. Cellular NF-"B activation was quantified in cell lysates 24 hours after transfection. Data of one representative experiment out of three (panels a, b, c and d) or two (panel e) are depicted.
Figure 6:
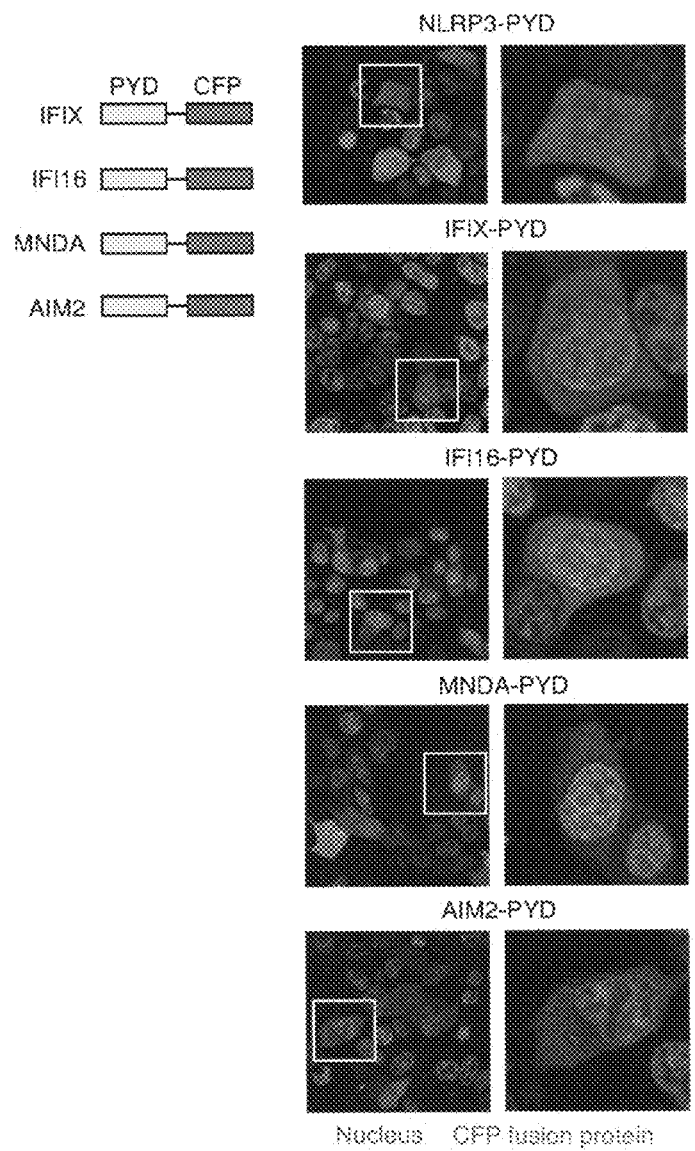
FIG. 6 shows that PYD-CFP fusion constructs of the PYHIN family are localized in the cytosol. 293T cells overexpressing CFP-tagged NLRP3-PYD, PYHIN1-PYD, PYHIN2-PYD, PYHIN3-PYD or AIM2-PYD (shown in green in the original) were analyzed by confocal microscopy, and nuclei were stained with DRAQ5 dye (shown in red in the original). Data from on representative experiments out of three are shown.
Figure 7:
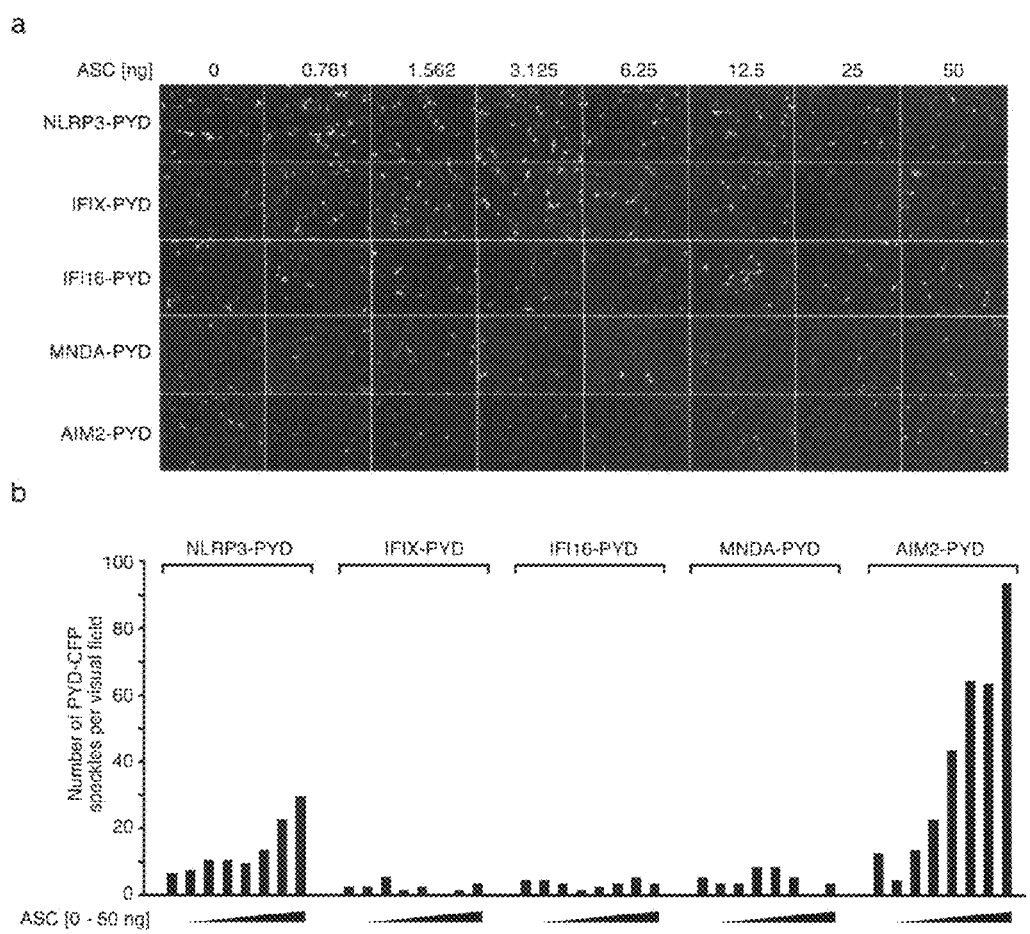
FIG. 7 shows that over expression of ASC induces complex formation of AIM2-PYD. 293T cells grown 96 well were transfected with fixed amounts of PYD-CFP fusion constructs (100 ng) together with increasing amounts of ASC-HA (0, 0.78, 1.56, 3.13, 6.25, 12.5, and 50 ng). 24 hours after transfection, cells were imaged by epifluorescence microscopy. Cluster formation of the PYD-CFP fusion constructs were quantified using ImageJ. The detected protein clusters of above-threshold fluorescence intensity are highlighted in red color (shown in red in the original) and overlaid on grayscale images of below threshold fluorescence intensity (non-clustered protein) (panel a). The absolute count of PYD-CFP clusters per visual field of a 20× objective as analyzed by ImageJ is shown in (panel b). One representative experiment out of three independent experiments is shown.
Figure 12:
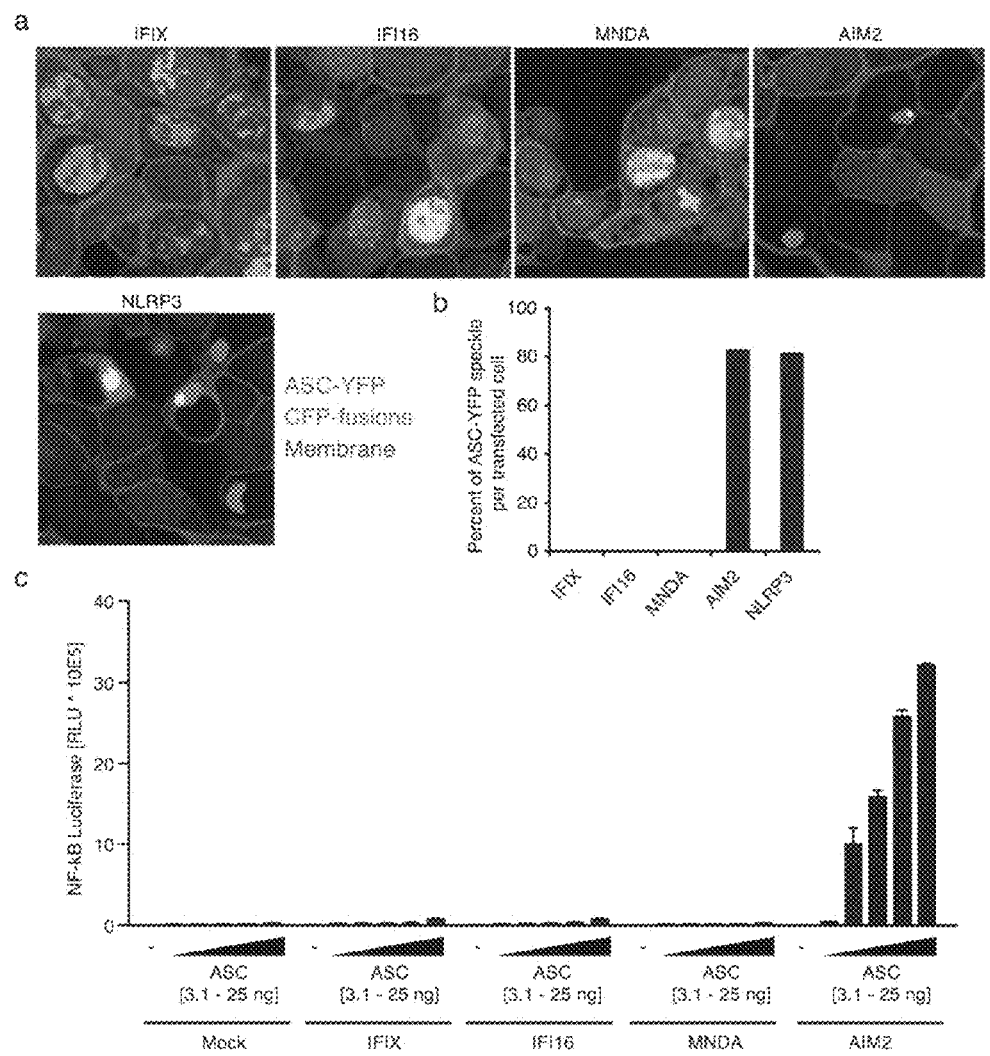
FIG. 12 shows that full length AIM2 induces complex formation of ASC and ASC-dependent NF-kappaB activation. a) Stable HEK293-ASC-YFP (shown in green in the original) cells were transiently transfected with CFP-tagged PYHIN-1, PYHIN-2, PYHIN-3, AIM2 or NLRP3 (all in red in the original), the membrane was stained with choleratoxin (shown in blue in the original) and cells were then imaged by confocal microscopy and the percentage of ASC-YFP speckles per transfected cells was assessed (panel b). c) 293T cells were transfected with a multimerized NF-kappaB luciferase reporter construct together with fixed amounts of constructs as in (a) alone or together with increasing amounts of ASC. Cellular NF-kappaB activation was quantified in cell lysates 24 hours after transfection. Data of one representative experiment out of two (panels a and b) or three (panel c) are depicted.

To study the possibility that these PYHIN proteins associated with ASC in the cytosol, C-terminally tagged CFP PYD-domain fusions were generated. Of note, the putative nuclear localization sequences were predicted to localize to the C-termini of these molecules. Consistent with these predictions, all of the PYD-CFP fusion proteins were localized in the cytoplasm and formed large cytosolic aggregates in a portion of the cells (FIG. 6). The cytosolic localization of the CFP-tagged PYD domains enabled study of the homotypic molecular interactions between overexpressed PYD domains of the PYHIN family proteins and ASC. To test whether induced clustering of PYD-CFP fusion proteins leads to association with ASC-YFP by homotypic pyrin-pyrin interactions, a HEK293 cell line that stably expressed ASC-YFP in the cytosol was utilized. This cell line expressed ASC-YFP at low enough levels to be polydispersed throughout the cytoplasm without visible aggregates (FIG. 2a, mock) allowing an analysis of proteins, which would induce ASC complex formation. Indeed, overexpression of the ASC-interacting NLRP3-CFP-tagged PYD domain led to the formation of large cytosolic aggregates, which co-aggregated ASC-YFP (FIG. 2a). Notably, in most transfected cells extensive co-localization with ASC-YFP was observed with a complete loss of cytoplasmic distribution of ASC-YFP. This observation is indicative of complete recruitment of ASC into the NLRP3-PYD complex (G. A. Manji, L. et al., The Journal of Biological Chemistry 277 (13), 11570 (2002); J. M. Grenier, et al., FEBS Lett 530 (1-3), 73 (2002); J. W. Yu, et al., Cell Death Differ 13 (2), 236 (2006)). Of all the PYHIN-PYD proteins tested, only AIM2-PYD led to complex formation with ASC (FIG. 2a and FIG. 7). Even though the overexpression of PYHINs 1-3 led to self-aggregation, no change in the expression pattern of ASC-YFP was observed. Expression of full-length AIM2-CFP similarly led to pronounced co-aggregation of ASC-YFP (FIG. 2a), while full length PYHINS 1-3 did not change the aggregation status of ASC-YFP (FIGS. 2a and b, and FIGS. 12a and b). In line with these results, only AIM2-PYD and NLRP3-PYD were found to bind ASC in co-immunoprecipitation studies from cells overexpressing the respective CFP-tagged PYD proteins together with HA-tagged ASC (FIG. 2c). Indeed, when endogenous ASC from primed THP-1 cells was immunoprecipitated, endogenous AIM2, but not PYHIN 2 was co-precipitated (FIG. 2d). These data indicated that the PYD domain of AIM2 but not that of PYHIN1-3 can physically interact with ASC and induce ASC pyroptosome formation.

Example 3

NF-kappaB Activation by AIM2-ASC Complex

Figure 8:
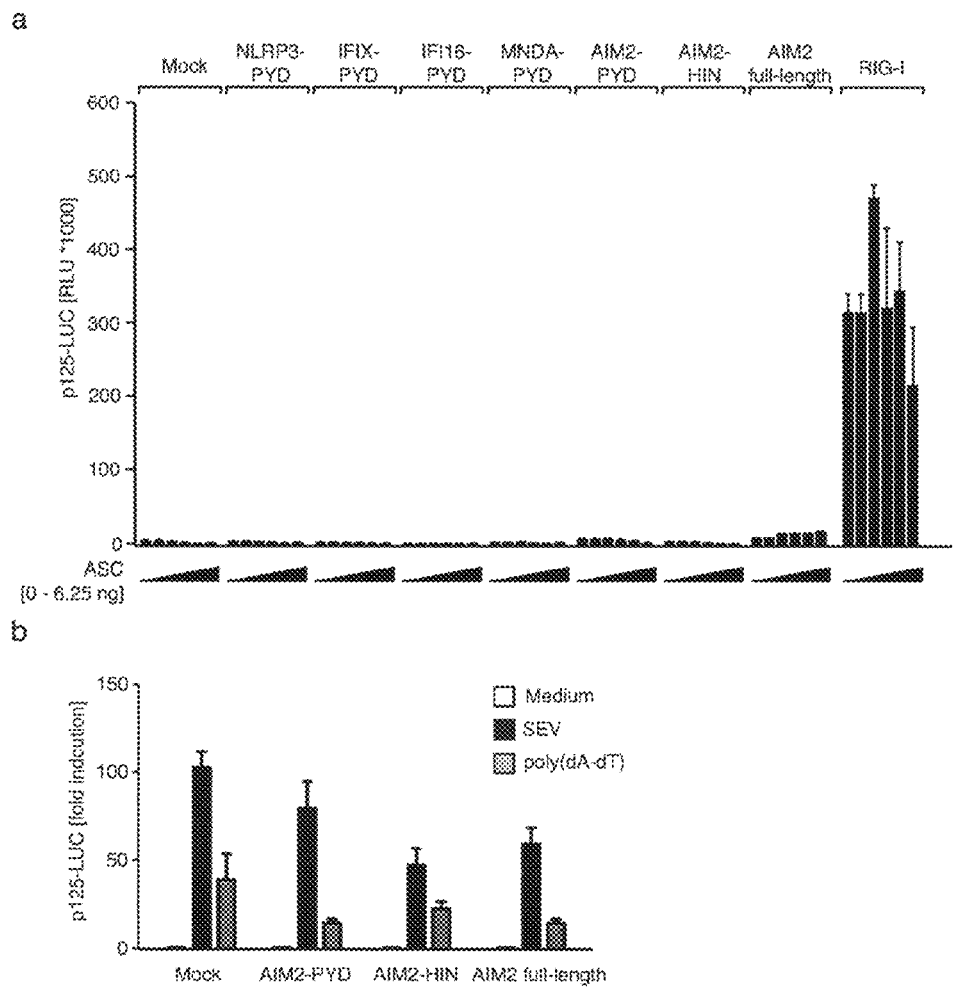
FIG. 8 shows that AIM2 is not involved in IFN induction. a) 293T cells grown in 96 well plates were transfected with a pIFN-beta luciferase reporter construct (p125-LUC) together with fixed amounts of NLRP3-PYD or PYHIN1-3 PYD-CFP fusion constructs, AIM2-PYD, AIM2HIN domain, AIM2 full length or RIG-I (100 ng) alone or together with increasing amounts of ASC. Transactivation of the IFN-beta promoter was quantified in cell lysates 24 hours after transfection. b) 293T cells were transfected with either AIM2-PYD, AIM2 HIN domain or AIM2 full length (100 ng) together with p125-LUC. 24 hours after transfection cells were re-transfected with 200 ng poly(dA-dT) and after an additional period of 24 hours, transactivation of the IFN-beta promoter was quantified in cell lysates by luminometry. Data of one representative experiment out of three are depicted as mean values+/−s.d.

Overexpression of ASC-interacting proteins can lead to the activation of both NF-kappaB and caspase-1 (G. A. Manji, et al., The Journal of Biological Chemistry 277 (13), 11570 (2002); S. M. Srinivasula, et al., The Journal of Biological Chemistry 277 (24), 21119 (2002)). To examine the functional relevance of AIM2-ASC complex formation, activation of an NF-kappaB reporter gene was studied in cells overexpressing the PYD-PYHIN proteins in the presence of increasing amounts of ASC. Consistent with the imaging and co-immunoprecipitation studies shown in Example 2, only NLRP3-PYD and AIM2-PYD led to potent NF-kappaB activation with increasing concentrations of ASC (FIG. 2e). The effect of full length AIM2 in this assay was even more dramatic, showing up to 60-fold increases in NF-kappaB activation in the presence of ASC (FIG. 2e, bottom panel). The full-length versions of PYHINs 1-3 failed to activate NF-kappaB (FIG. 12c). ASC was shown to be involved in NF-kappaB activation, since in 293T cells not transfected with ASC, no significant NF-kappaB reporter activity was observed. IFN-beta gene induction was also observed in these assays and in contrast to what we saw with NF-kappaB signaling, no significant activation of the IFN-beta promoter reporter gene with any of the PYHIN family members was found (FIG. 8). Altogether, these results indicated that AIM2 is unique amongst the PYHIN family by being localized to the cytosol, interacting with ASC leading to cytosolic pyropotosome complex formation and subsequent NF-kappaB activation.

Example 4

Formation of a Functional Inflammasome Complex and pro-IL-1beta Maturation

Figure 3:
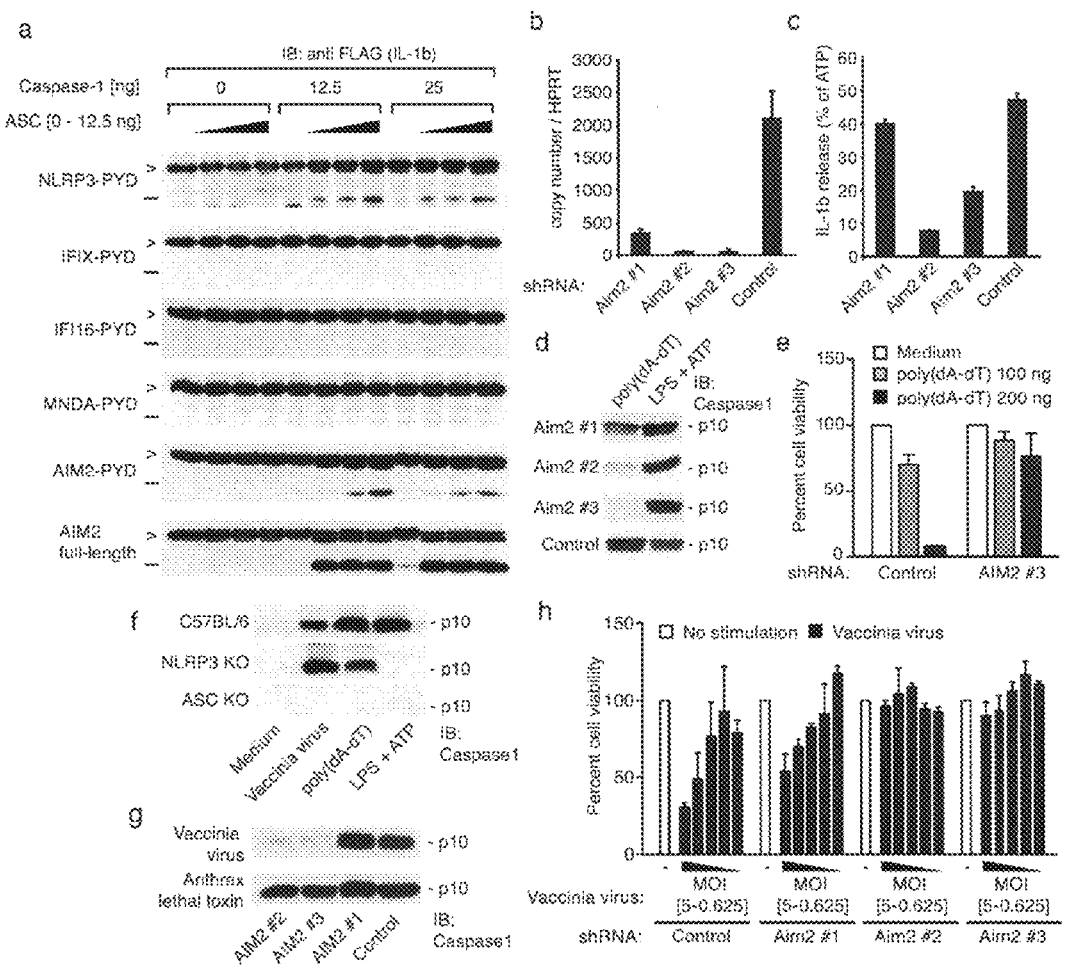
FIG. 3 shows that AIM2 is involved in poly(dA-dT) triggered inflammasome activation. a) 293T cells were transfected with caspase-1 (12.5 or 25 ng), ASC (3.1, 6.2 or 12.5 ng), pro-IL-1beta (100 ng) and NLRP3-PYD, PYHIN-1, PYHIN-2 and PYHIN-3-PYD, PISA-PYD or AIM2 full length (50 ng). Cell lysates were immunoblotted for the C-terminally tagged IL-1beta, recognizing both pro-IL-1beta (>) and cleaved IL-1beta (−) 24 h after transfection. b) Murine macrophage cells (B6-MCLs) were transduced with lentiviral vectors encoding shRNAs targeting AIM2 (AIM2#1, AIM2#2, AIM2#3) or an irrelevant control gene (Ctrl.). PISA/HPRT1 expression was determined in shRNA expressing cells. c) Cells as in (b) were primed with LPS and then stimulated with poly(dA-dT) or ATP. After 6 h supernatants were assessed for IL-1beta by ELISA. The poly(dA-dT) triggered IL-1beta release was normalized to the respective ATP induced IL-1beta release. The absolute values for the ATP-triggered IL-1beta release were 1790, 2078, 2676 and 1119 pg/ml (AIM2#1, AIM2#2, AIM2#3 and Control) respectively (b). d) In addition, murine macrophages as in (b) were transfected with poly(dA-dT) or stimulated with LPS/ATP and assessed for cleavage of caspase-1 after 6 h. e) Murine macrophages transduced with shRNA targeting AIM2 (AIM#3) or an irrelevant control gene (Ctrl.) were transfected with 200 ng poly(dA-dT) or 100 ng poly(dAdT) and cell counts were assessed 24 h after transfection. f) Macrophages from either wild type, ASC−/− or NLRP3−/− were infected with vaccinia virus, transfected with poly(dA-dT) or stimulated with LPS/ATP and assessed for cleavage of caspase-1 after 6 h. g) NLRP3-deficient shRNA expressing murine macrophages as in (b) were infected with vaccinia virus or stimulated with Anthrax lethal toxin and assessed for cleavage of caspase-1 after 6 h. h) Cells as in (b) were infected with ascending doses of vaccinia virus (MOI 0.625-5) and cell survival was determined by calcein AM staining 24 h after infection. One representative experiment out of three (panels a, d, e, f, g and h) four (panel c) or five (panel b) is depicted.
Figure 9:
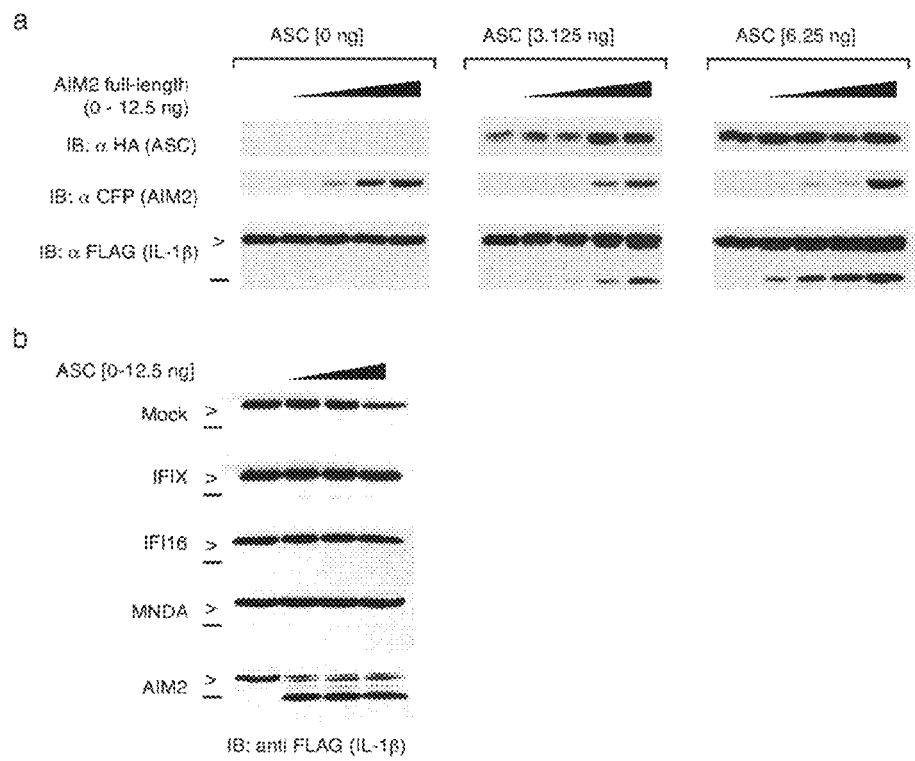
FIG. 9 shows that low level expression of full length AIM2 induces robust cleavage of IL-1beta. 293T cells were transfected with caspase-1 (12.5 ng), ASC (3.1 or 6.25 ng), pro-IL-1beta (100 ng) and ascending amounts of AIM2 full length (1.56, 3.12, 6.25, 12.5 ng). Cell lysates were immunoblotted for ASC expression (HA epitope), AIM2 expression (CFP tag) and the C-terminally epitope tagged IL-1beta, recognizing both the pro-IL-1beta form (>) and the cleaved IL-1beta form (−) 24 h after transfection. b) 293T cells were transfected with caspase-1 (12.5 ng), ASC (6.25 ng), pro-IL-1beta (100 ng) and either full length PYHIN-1, PYHIN-2, PYHIN-3 or AIM2 (81.25 ng) and analyzed as in (a). One representative experiment out of two is depicted (panels a and b).

It was next determined whether the AIM2-ASC complex formation led to formation of a functional inflammasome complex and caspase-1 dependent maturation of pro-IL-1beta. A transient transfection assay overexpressing the respective proteins of interest in the presence of ASC, caspase-1 and a Flag-tagged version of pro-IL-1beta in 293T cells was employed. In this experimental setup, the cleavage of pro-IL-1beta into IL-1beta was assessed in the cell lysate by immunoblot analysis. Among the PYD proteins tested, only NLRP3-PYD and AIM2-PYD induced maturation of pro-IL-1beta when ASC and caspase-1 were coexpressed (FIG. 3a). Expression of full length AIM2 induced a robust cleavage of pro-IL-1beta even in the presence of only minute amounts of ASC and caspase-1 when compared to AIM2-PYD (FIG. 3a, lower panel). Moreover, only a very low level expression of full length AIM2 was required to induce cleavage of pro-IL-1beta in the presence of ASC and caspase-1, while the PYD domain or full length versions of PYHINS 1-3 failed to induce IL-1beta cleavage (FIG. 9). These results indicated that AIM2-ASC complex formation led to formation of a functional inflammasome complex and caspase-1 dependent maturation of pro-IL-1beta.

Example 5

Effects of an shRNA-Induced Decrease in AIM2 Expression

Figure 10:
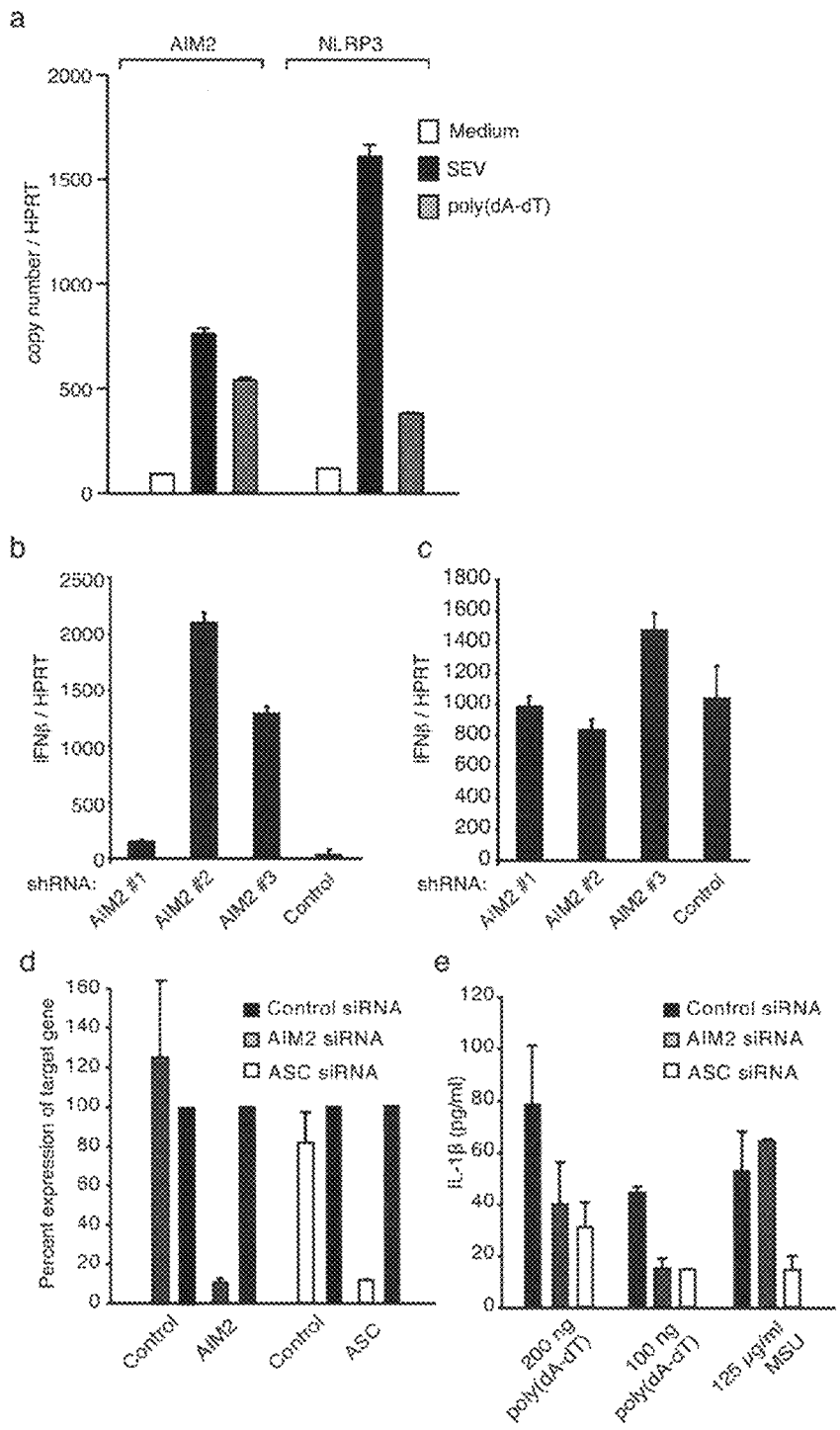
FIG. 10 shows that knock down of AIM2 expression enhances poly(dAdT) triggered type I IFN production. a) Macrophages from wild type mice were transfected with poly(dA-dT) or stimulated with sendai virus (300 HAU/ml). After 5 hours, AIM2, NLRP3 and HPRT1 mRNA expression was determined by real time PCR. The expression levels were normalized to HPRT1 expression. Murine macrophage cells (B6-MCLs) were transduced with lentiviral vectors encoding shRNAs targeting AIM2 (AIM2#1, AIM2#2, AIM2#3) or an irrelevant control gene (Ctrl.) and were stimulated with either poly(dA-dT) (panel b) or Sendai virus (300 HAU/ml) (panel c) and IFN-beta/HPRT1 expression was determined after 5 h. d) siRNAs targeting human AIM2, ASC or TLR8 (Control siRNA) were cotransfected into 293T cells with expression plasmids coding for either AIM2-CFP or ASC-CFP, whereas MNDA-CFP served as a control target (Control). 24 h after transfection, CFP expression was assessed by FACS and is depicted as percent expression in relation to the control siRNA. e) THP1 cells were transfected with siRNA targeting TLR8 (Control), AIM2 or ASC. 48 h after transfection, cells were stimulated with 200 or 100 ng poly(dA-dT) or 125 µg/ml MSU crystals. 6 h after stimulation IL-1-beta production was assessed by ELISA. One representative experiment out of two (panels a, d and e) or four (panels b and c) independent experiments is depicted as mean values+/−s.d.

To study the role of AIM2 in cells with a functional poly (dA-dT)-triggered inflammasome complex, lentiviruses encoded shRNAs were used to decrease AIM2 expression in a murine macrophage cell line generated by immortalizing C57/B16 bone marrow derived macrophages (B6-MCL) or NLRP-3-deficient mice (N-3-KO-MCLs) (V. Hornung, et al., Nat Immunol 9 (8), 847 (2008)). AIM2 was expressed constitutively in both primary murine macrophages and in B6-MCLs, and was inducible upon stimulation with poly (dA-dT) or with the paramyxovirus Sendai virus (FIG. 10). Three different shRNAs were used to decrease AIM2 expression, of which two (shRNA AIM2#2 and AIM2#3) resulted in a strong reduction of AIM2 expression as determined by real time PCR (FIG. 3b). Reduction of AIM2 expression, but not an unrelated control gene, resulted in a strong attenuation of poly(dA-dT)-mediated IL-1beta release (FIG. 3c) and caspase cleavage (FIG. 3d). Targeting AIM2 in THP1 cells using siRNA corroborated these findings (FIGS. 10d and e). Moreover and consistent with what we had seen in ASC-deficient macrophages (FIG. 5), reducing AIM2 expression resulted in a marked enhancement of poly(dA-dT)-mediated type I IFN induction (FIG. 10b). This effect was not seen with Sendai virus since the IFN-beta response to Sendai virus was unaffected when AIM2 levels were reduced by shRNA (FIG. 10c). In addition, and in agreement with the results obtained in ASC-deficient macrophages, macrophages that were targeted with AIM2-targeting shRNAs were strongly resistant to poly(dA-dT) triggered cell death (FIG. 3e). These results indicated that AIM2 was involved in poly(dA-dT)-mediated inflammasome activation and that AIM2 negatively regulated the poly(dA-dT)-mediated type I IFN-response.

Example 6

Effects of an shRNA-Induced Decrease on Cell Death

To study the effect of AIM2 on the recognition of a dsDNA virus, mouse macrophages from wild-type, NLRP3- and ASC-deficient mice were infected with vaccinia virus and caspase-1 cleavage was monitored. Similarly to what was observed with sensing of transfected poly(dA-dT), vaccinia virus-induced caspase-1 cleavage occurred in an NLRP3-independent, yet ASC-dependent fashion (FIG. 30. This effect was dependent on AIM2, since shRNA-mediated knock down of AIM2 greatly impaired caspase-1 cleavage in response to vaccinia virus but not in response to an AIM2-independent stimulus. Moreover, knock down of a control protein did not alter caspase-1 cleavage after vaccinia virus infection (FIG. 3g). Vaccinia virus-triggered cell death was also strongly reduced in AIM2 shRNA targeted macrophages, but not in control shRNA targeted macrophages (FIG. 3h).

Figure 11:
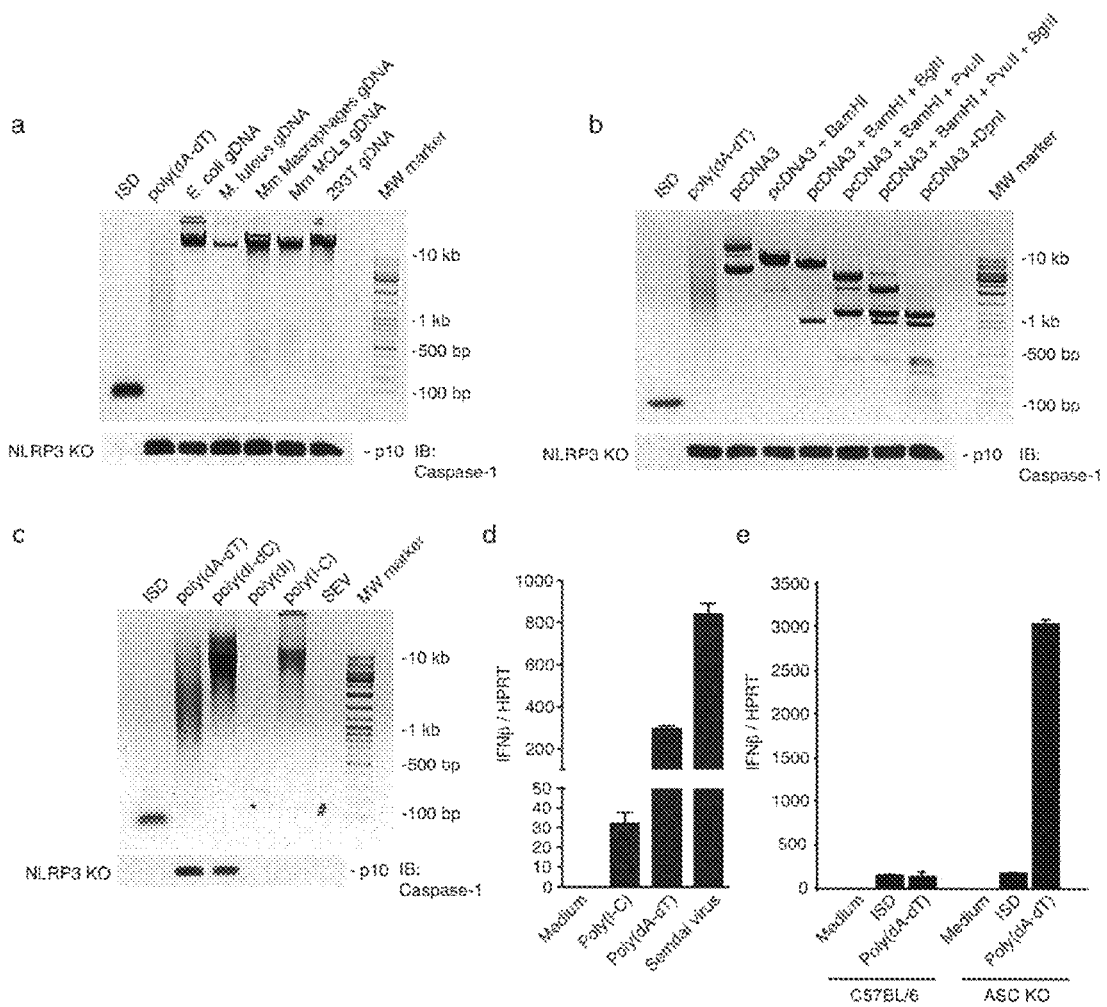
FIG. 11 shows that dsDNA from prokaryotic and eukaryotic sources activates caspase-1 independent of NLRP3. a) NLRP3-deficient macrophages were transfected with the dsDNA oligonucleotide immune stimulatory DNA (ISD), poly(dA-dT), genomic DNA from *Escherichia coli* (gram negative bacteria), genomic DNA from *Micrococcus luteus* (gram positive bacteria), genomic DNA from primary macrophages, genomic DNA from immortalized macrophages or genomic DNA from 293T cells. 6 h after stimulation caspase-1 cleavage was assessed by immunoblot (lower panel). b) NLRP3-deficient macrophages were transfected with ISD, poly(dA-dT) or pcDNA3 undigested or digested to yield a maximal dsDNA product of either 5446 bp (BamHI), 4551 bp (BamHI and BglII), 2899 bp (BamHI and PvuII), 2004 bp (BamHI, PvuII and BglII) or 1108 bp (DpnI). 6 h after stimulation caspase-1 cleavage was assessed by immunoblot (lower panel). c) NLRP3-deficient macrophages were transfected with ISD, poly(dA-dT), poly(dI-dC), poly(dI), poly(I-C) or infected with Sendai virus. 6 h after stimulation caspase-1 cleavage was assessed by immunoblot. All nucleic acids (a, b, and c) were separated on a 1% agarose gel and stained with ethidium bromide (upper panels). Of note, the single stranded homopolymer poly(dI) (*) could not be visualized using this technique given that ethidium bromide only intercalates in double stranded nucleic acids. d) Wild type macrophages were transfected with poly(I-C), poly(dA-dT) or infected with Sendai virus. In addition, wild type macrophages or NLRP3-deficient macrophages were transfected with ISD or poly(dA-dT) (panel e). After 5 h, IFN-beta and HPRT1 mRNA expression was determined by real time PCR, whereas IFN-beta expression levels were normalized to HPRT1 expression. Data from one representative experiment (panels a, b, c, d and e) out of two are shown.

Without wishing to be bound by theory, we speculate that the increased cytokine production observed in ASC-deficient cells relates to their resistance to poly(dA-dT) induced cell death. In addition to poly(dA-dT), dsDNA from natural sources also activated this response (FIG. 11a-b). In contrast, a small immunostimulatory oligonucleotide (ISD) (Stetson and Medzhitov, *Immunity* 24(1), 93 (2006)) or long ssDNA (poly(dI)) failed to trigger caspase-1 cleavage. Moreover, the ssRNA virus Sendai virus or transfected dsRNA also failed to induce caspase-1 cleavage in NLRP3-deficient macrophages (FIG. 11c).

These results indicated that AIM2 positively regulated dsDNA and vaccinia virus-triggered cell death.

Example 7

Involvement of AIM2 in the Recognition of dsDNA

Figure 4:
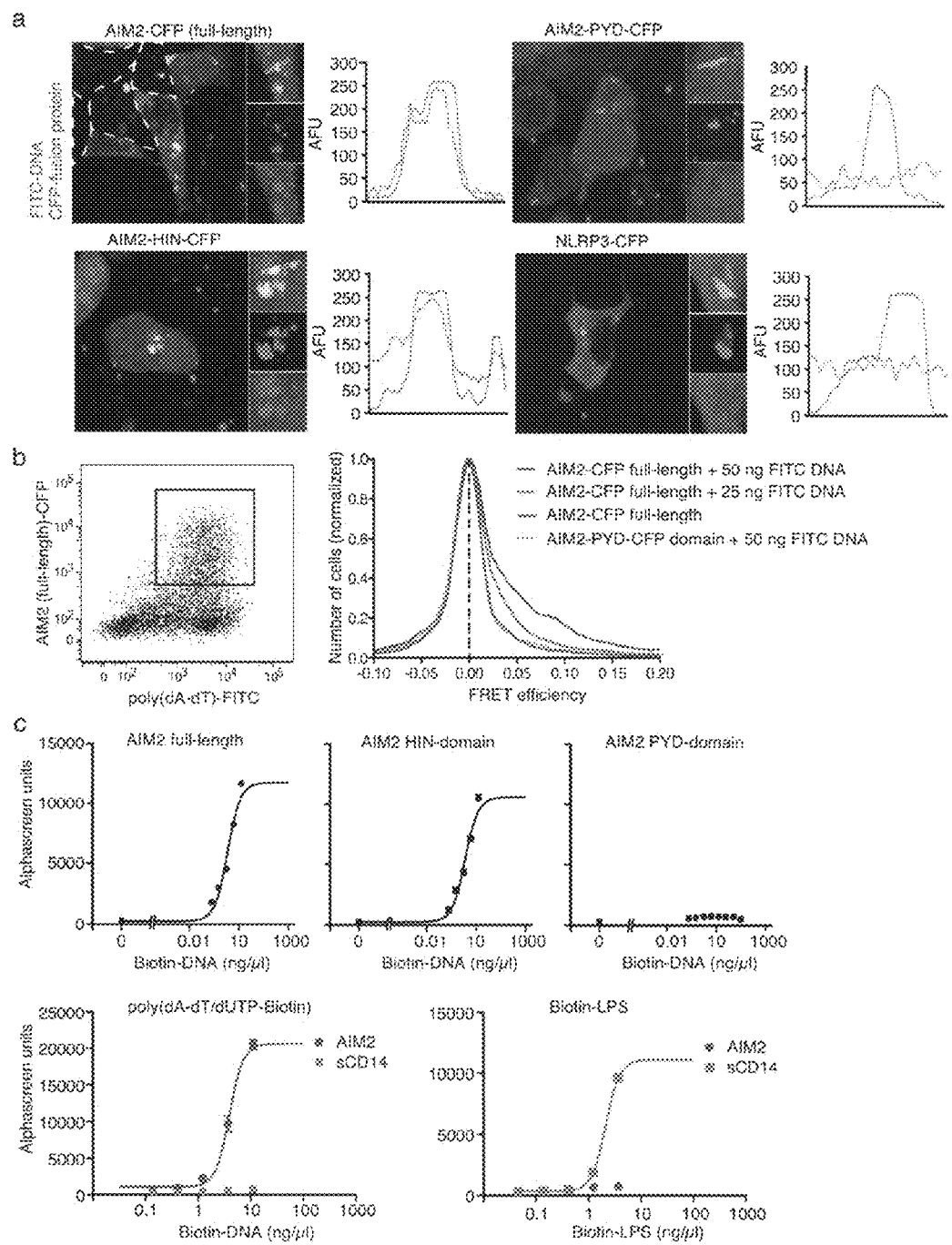
FIG. 4 shows that AIM2 binds dsDNA via its HIN domain. a) 293T cells were transfected with expression plasmids encoding CFP-tagged AIM2-full length, AIM2-HIN, AIM2-PYD, and NLRP3 (shown in red in the original) together with fluorescein labeled poly(dA-dT) (FITC-DNA, shown in green in the original). Cells were analyzed by confocal microscopy 24 h after transfection. Fluorescence intensities of the green (FITC-DNA) and red (CFP fusion protein) channels (green and red shown in the original) were quantified along selected lines (white lines). b) 293T cells were transfected with either CFP-tagged PIDA full-length or AIM2-PYD and FITC-DNA or unlabeled DNA. Cells were analyzed by flow cytometry after 24 h and CFP and FITC positive cells were gated (left panel) and analyzed for FRET efficiency on a cell-by-cell basis. Calculated FRET efficiency histograms are shown (right panel). c) AlphaScreen (homogenous ligand-binding assay) assessment of AIM2 full length, AIM2-HIN domain or AIM2-PYD domain binding to poly(dA-dT)/Biotin-dUTP (Biotin-DNA) (upper panel) AlphaScreen assay of AIM2 or sCD14 binding to Biotin-DNA or biotin LPS (lower panel). Representative data from 2 (panel d) or three (panels a, b, c) independent experiments are shown.

AIM2 harbors a C-terminal HIN200 domain, which type of domain was previously shown to bind dsDNA. To examine if AIM2 could be directly involved in the recognition of dsDNA, fluorescein labeled poly(dA-dT) (FITC-DNA) was generated and co-transfected together with CFP-tagged versions of full length AIM2, AIM2 HIN-domain, AIM2 pyrin domain or full-length NLRP3. While cells expressing NLRP3 or AIM2-PYD showed no co-localization of the respective proteins with FITC-DNA, full length AIM2 and AIM2-HIN showed extensive co-localization with FITC-dsDNA and led to the formation of DNA/protein aggregate complexes (FIG. 4a). To quantitate these DNA/protein interactions, the interaction of AIM2 with FITC-poly(dA-dT) was analyzed by fluorescence resonance energy transfer (FRET) measurements using flow cytometry (FIG. 4b). Dose-responsive increases in FRET between the full length AIM2 protein and FITC-DNA were observed, while the AIM2-PYD protein did not lead to FRET. Other proteins like NLRP3 or PYHIN2 (data not shown) did not show any FRET even at the highest concentration of FITC-DNA. Additionally, binding studies using purified AIM2, AIM2-HIN and AIM2-PYD proteins with biotinylated poly(dA-dT) (biotin-DNA) demonstrated that AIM2 directly interacts with poly(dA-dT) with high affinity; only full length AIM2 or AIM2-HIN were able to bind biotin-DNA, whereas no binding was observed for AIM2-PYD (FIG. 4c). Binding of poly(dA-dT) to AIM2 was specific, since AIM2 did not bind biotin-LPS, which bound to soluble CD14 under similar assay conditions (FIG. 4c). These results indicated that AIM2 is directly involved in the recognition of dsDNA.

Certain patent and non-patent documents are cited herein. These documents are hereby incorporated by reference in their entirety. To the extent that any part of the disclosures of any of these documents conflicts with teachings or discoveries presented herein, the teachings or discoveries of the present document will control.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of identifying a compound that modulates an AIM2 polypeptide-mediated immune response, the method comprising:
   (a) providing a cell that expresses an exogenous AIM2 polypeptide comprising a pyrin (PYD) domain;
   (b) contacting the cell with a test compound to generate a test sample;
   (c) incubating the test sample under conditions and for a time sufficient such that the AIM2 polypeptide and an apoptosis-associated speck-like protein containing a caspase recruitment domain (ASC polypeptide) would co-localize intracellularly if a reference sample lacking the test compound were incubated under said conditions and for said time; and
   (d) detecting a level of intracellular co-localization of the AIM2 polypeptide and the ASC polypeptide;
   wherein a change in the level of intracellular co-localization of the AIM2 polypeptide and the ASC polypeptide in the test sample compared to said reference sample indicates that the test compound is a compound that modulates the AIM2 polypeptide-mediated immune response.

2. The method of claim 1, wherein the AIM2 polypeptide is labeled.

3. The method of claim 1, wherein the AIM2 polypeptide is a fusion polypeptide.

4. The method of claim 1, wherein the AIM2 polypeptide is a fluorescent fusion polypeptide.

5. The method of claim 1, wherein the AIM2 polypeptide is a fusion protein comprising a Yellow Fluorescent Protein (YFP), a Cyan Fluorescent Protein (CFP), Green Fluorescent Protein (GFP), Red Fluorescent Protein (RFP), or a fluorescent variant thereof.

6. The method of claim 1, wherein the ASC polypeptide is labeled.

7. The method of claim 1, wherein the ASC polypeptide is a fusion protein.

8. The method of claim 1, wherein the ASC polypeptide is a fluorescent fusion protein.

9. The method of claim 1, wherein the ASC polypeptide is a fusion protein comprising a Yellow Fluorescent Protein (YFP), a Cyan Fluorescent Protein (CFP), Green Fluorescent Protein (GFP), Red Fluorescent Protein (RFP), or a fluorescent variant thereof.

10. A method of identifying a compound that modulates an AIM2 polypeptide-mediated immune response, the method comprising:
    (a) providing a cell that expresses an exogenous AIM2 polypeptide;
    (b) contacting the cell with a test compound to generate a test sample;
    (c) incubating the test sample under conditions and for a time sufficient such that a cellular characteristic of an AIM2 polypeptide-mediated immune response would occur if a reference sample lacking the test compound were incubated under said conditions and for said time; and
    (d) detecting the cellular characteristic, wherein the cellular characteristic is selected from the group consisting of: cleavage of a pro-IL-1beta polypeptide, expression of NF-kappaB, and type I IFN induction;
    wherein a change in the detected cellular characteristic compared to a reference cellular characteristic that would be observed in said reference sample indicates that the test compound is a compound that modulates the AIM2 polypeptide-mediated immune response.

11. The method of claim 10, wherein the detected cellular characteristic comprises cleavage of a pro-IL-1beta polypeptide, and wherein the pro-IL-1beta polypeptide is a pro-IL-1beta fusion polypeptide.

12. The method of claim 11, wherein the pro-IL-1beta fusion polypeptide comprises an epitope tag.

13. The method of claim 12, wherein the epitope tag is selected from the group consisting of a Flag, myc, T7, Glutathione-S-transferase, Yellow Fluorescent Protein (YFP), a Cyan Fluorescent Protein (CFP), Green Fluorescent Protein (GFP), Red Fluorescent Protein (RFP), hemagglutinin, and combinations thereof.

14. A method of identifying a compound that modulates an AIM2 polypeptide-mediated immune response, the method comprising:
    (a) providing a cell that expresses an exogenous AIM2 polypeptide comprising a HIN200 domain;
    (b) contacting the cell with a test compound to generate a test sample;
    (c) incubating the test sample under conditions and for a time sufficient such that the AIM2 polypeptide and a cytoplasmic dsDNA would co-localize intracellularly if a reference sample lacking the test compound were incubated under said conditions and for said time; and
    (d) detecting a level of intracellular co-localization of the AIM2 polypeptide and the cytoplasmic dsDNA;
    wherein a change in the level of intracellular co-localization of the AIM2 polypeptide and the cytoplasmic dsDNA compared to said reference sample indicates that the test compound is a compound that modulates the AIM2 polypeptide-mediated immune response.

15. The method of claim 14, wherein the AIM2 polypeptide is labeled.

16. The method of claim 14, wherein the AIM2 polypeptide is a fusion polypeptide.

17. The method of claim 14, wherein the AIM2 polypeptide is a fluorescent fusion polypeptide.

18. The method of claim 14, wherein the AIM2 polypeptide is a fusion protein comprising a Yellow Fluorescent Protein (YFP), a Cyan Fluorescent Protein (CFP), Green Fluorescent Protein (GFP), Red Fluorescent Protein (RFP), or a fluorescent variant thereof.

19. The method of claim 14, wherein the cytoplasmic dsDNA is labeled with a fluorophore.

20. The method of claim 19, wherein the fluorophore is selected from the group consisting of: fluorescein, 6-FAM, TET, HEX, TAMRA, Texas Red, JOE, Cy5, Cy3, BODIPY FL, Oregon Green 488, and combinations thereof.

* * * * *